(12) United States Patent
Peterka

(10) Patent No.: US 7,727,162 B2
(45) Date of Patent: Jun. 1, 2010

(54) BIAS-PROBE ROTATION TEST OF VESTIBULAR FUNCTION

(75) Inventor: Robert J. Peterka, Portland, OR (US)

(73) Assignee: Oregon Health & Science University, Portland, OR (US)

(*) Notice: Subject to any disclaimer, the term of this patent is extended or adjusted under 35 U.S.C. 154(b) by 0 days.

(21) Appl. No.: 11/974,165

(22) Filed: Oct. 11, 2007

(65) Prior Publication Data

US 2008/0045812 A1 Feb. 21, 2008

Related U.S. Application Data

(62) Division of application No. 10/762,211, filed on Jan. 21, 2004, now Pat. No. 7,285,099.

(60) Provisional application No. 60/441,853, filed on Jan. 21, 2003.

(51) Int. Cl.
*A61B 5/00* (2006.01)
*A61B 19/00* (2006.01)
(52) U.S. Cl. .................. 600/559; 600/552; 600/553
(58) Field of Classification Search .......... 600/552, 600/553, 558, 559
See application file for complete search history.

(56) References Cited

U.S. PATENT DOCUMENTS

| | | | |
|---|---|---|---|
| 3,000,271 A | 9/1961 | Harvey et al. | |
| 3,258,008 A | 6/1966 | Vulliet-Durand | |
| 3,716,046 A | 2/1973 | Janeke | |
| 4,474,186 A | 10/1984 | Ledley et al. | |
| 4,702,576 A * | 10/1987 | Magnante | 351/214 |
| 5,303,715 A | 4/1994 | Nashner et al. | |
| 5,517,021 A * | 5/1996 | Kaufman et al. | 250/221 |
| 5,942,954 A | 8/1999 | Galiana et al. | |
| 6,089,714 A * | 7/2000 | Galiana et al. | 351/202 |
| 6,120,461 A * | 9/2000 | Smyth | 600/558 |
| 6,231,187 B1 * | 5/2001 | Munoz et al. | 351/209 |
| 6,661,345 B1 * | 12/2003 | Bevan et al. | 340/575 |
| 6,800,062 B2 | 10/2004 | Epley | |
| 7,285,099 B1 | 10/2007 | Peterka | |
| 2002/0151818 A1 | 10/2002 | Watt et al. | |
| 2004/0097839 A1 | 5/2004 | Epley | |

OTHER PUBLICATIONS

Aw, S T., "Head impulses reveal loss of individual semicircular canal function", *Journal of Vestibular Research*, 9(3), (1999),173-80.

(Continued)

*Primary Examiner*—Max Hindenburg
*Assistant Examiner*—Sean P Dougherty
(74) *Attorney, Agent, or Firm*—Schwegman Lundberg & Woessner, P.A.

(57) ABSTRACT

Apparatus and methods for rotation test stimulus and analysis methods overcome many of the limitations of traditional clinical tests of peripheral vestibular function. An embodiment includes a rotational stimuli applied to the rotational motion for testing that includes two separate components, a bias component and a probe component. The bias component for rotational motion is designed to temporarily turn off vestibular responses in one ear while the responsiveness in the opposite ear is simultaneously evaluated using the probe component of the stimulus. Responses from application of these stimuli are analyzed by isolating and separating the bias response from the probe response. The bias and probe component responses are parameterized by applying curve fits of mathematical functions to the isolated bias and probe component responses. These parameters characterize the patient's vestibular function.

9 Claims, 18 Drawing Sheets

OTHER PUBLICATIONS

Aw, S T., et al., "Three-dimensional vector analysis of the human vestibuloocular reflex in response to high-acceleration head rotations. II. responses in subjects with unilateral vestibular loss and selective semicircular canal occlusion", *Journal of Neurophysiology*, 76(6), (Dec. 1996),4021-30.

Baloh, R W., et al., "Changes in the human vestibulo-ocular reflex after loss of peripheral sensitivity", *Annals of Neurology*, 16(2), (Aug. 1984),222-8.

Baloh, Robert W., et al., "Clinical Evaluation of Hearing (Ch.6) & Differential Diagnosis of Vestibular System Disease (Ch.7)", *In. Clinical Neurophysiology of the Vestibular System*, Contemporary Neurology Series, P.A. Davis Company, Philadelphia, PA.,(1979),pp. 153-173.

Baloh, R W., et al., "Impulsive and sinusoidal rotatory testing: a comparison with results of caloric testing", *Laryngoscope*, 89(4), (Apr. 1979),646-54.

Benson, A J., "Motion Sickness", *In: Vertigo* / edited by M.R. Dix and J.D. Hood, Chichester ; New York : Wiley,(1984),391-426.

Beynon, G J., et al., "A clinical evaluation of head impulse testing", *Clinical Otolaryngology & Allied Sciences*, 23(2), (Apr. 1998),117-22.

Black, F O., et al., "Effects of unilateral loss of vestibular function on the vestibulo-ocular reflex and postural control", *Annals of Otology, Rhinology & Laryngology*, 98(11), (Nov. 1989),884-9.

Blanks, R H., et al., "Planar relationships of the semicircular canals in man", *Acta Otolaryngol* (Stockholm), 80, (1975),185.

Bouveresse, A , et al., "Pseudorandom rotational stimuli of the vestibulo-ocular reflex in humans: normal values of the transfer function", *Acta Oto-Rhino-Laryngologica Belgica*, 52(3), (1998),207-14.

Clarke, A H., et al., "Video-oculography-an alternative method for measurement of three-dimensional eye movements", *In: Oculomotor control and cognitive processes : normal and pathological aspects /* edited by Roberto Schmid and Daniela Zambarbieri., Amsterdam ; New York : North-Holland ; New York, N.Y. U.S.A.,(1991),431-443.

Cleveland, W S., "Robust locally weighted regression and smoothing scatterplots", *Journal of the American Statistical Association*, 74(368,(1979),829-836.

Crane, B T., et al., "Human horizontal vestibulo-ocular reflex initiation: effects of acceleration, target distance, and unilateral deafferentation", *Journal of Neurophysiology*, 80(3), (Sep. 1998),1151-66.

Curthoys, I S., et al., "Semicircular duct and ampulla dimensions in cat, guinea pig and man", *Journal of Morphology*, 151(1), (Jan. 1977),17-34.

Curthoys, I S., et al., "Vestibular compensation: a review of the oculomotor, neural, and clinical consequences of unilateral vestibular loss", *Journal of Vestibular Research*, 5(2), (Mar.-Apr. 1995),67-107.

Fernandez, C , et al., "Physiology of peripheral neurons innervating semicircular canals of the squirrel monkey. II. Response to sinusoidal stimulation and dynamics of peripheral vestibular system", *Journal of Neurophysiology*, 34(4), (Jul. 1971),661-75.

Fetter, M , et al., "Recovery from unilateral labyrinthectomy in rhesus monkey", *Journal of Neurophysiology*, 59(2), (Feb. 1988),370-93.

Foster, C A., et al., "Functional loss of the horizontal doll's eye reflex following unilateral vestibular lesions", *Laryngoscope*, 104(4), (Apr. 1994),473-8.

Furman, J M., et al., "Interlaboratory variability of rotational chair test results II: analysis of simulated data.", *Otolaryngology—Head & Neck Surgery*, 122(1), .[erratum appears in Otolaryngol Head Neck Surg Nov. 2001;125(5):580],(Jan. 2000),23-30.

Furman, J M., et al., "Laboratory evaluation. I: Electronystagmography and rotational testin.", *In: Disorders of the vestibular system* / edited by Robert W. Baloh, G. Michael Halmagyi, New York : Oxford University Press,(1996),191-210.

Galiana, H L., et al., "A bilateral model for central neural pathways in vestibuloocular reflex", *Journal of Neurophysiology*, 51(2), (Feb. 1984),210-41.

Galiana, H L., "A nystagmus strategy to linearize the vestibulo-ocular reflex", *IEEE Transactions on Biomedical Engineering*, 38(6), (Jun. 1991),532-43.

Galiana, H L., et al., "A reevaluation of intervestibular nuclear coupling: its role in vestibular compensation", *Journal of Neurophysiology*, 51(2), (Feb. 1984),242-59.

Goldberg, J M., et al., "Physiology of peripheral neurons innervating semicircular canals of the squirrel monkey. 3. Variations among units in their discharge properties", *Journal of Neurophysiology*, 34(4), (Jul. 1971),676-84.

Goldberg, J M., et al., "Physiology of peripheral neurons innervating semicircular canals of the squirrel monkey. I. Resting discharge and response to constant angular accelerations", *Journal of Neurophysiology*, 34(4), (Jul. 1971),635-60.

Graybiel, A , et al., "Diagnostic criteria for grading the severity of acute motion sic", *Aerospace Medicine*, 39(5), (May 1968),453-5.

Guyot, J P., et al., "Test-retest reliability of vestibular autorotation testing in healthy subjects", *Otolaryngology—Head & Neck Surgery*, 117(6), (Dec. 1997),704-7.

Halmagyi, G M., et al., "A clinical sign of canal paresis", *Archives of Neurology*, 45(7), (Jul. 1988),737-9.

Haslwanter, T , "Mathematics of three-dimensional eye rotations", *Vision Research*, 35(12), (Jun. 1995),1727-39.

Hatamian, M , et al., "Design considerations for a real-time ocular counterroll instrument", *IEEE Transactions on Biomedical Engineering*, 30(5), (May 1983),278-88.

Henry, D F., et al., "Closed-loop caloric, harmonic acceleration and active head rotation tests: norms and reliability", *Otolaryngology—Head & Neck Surgery*, 109(6), (Dec. 1993),975-87.

Honrubia, V , et al., "Vestibulo-ocular reflexes in peripheral labyrinthine lesions: I. Unilateral dysfunction", *American Journal of Otolaryngology*, 5(1), (Jan.-Feb. 1984),15-26.

Honrubia, V , et al., "Vestibulo-ocular reflexes in peripheral labyrinthine lesions: III. Bilateral dysfunction.", *American Journal of Otolaryngology*, 6(5), (Sep.-Oct. 1985),342-52.

Jenkins, H A., et al., "Evaluation of multiple-frequency rotatory testing in patients with peripheral labyrinthine weakness", *American Journal of Otolaryngology*, 3(3), (May-Jun. 1982),182-8.

Jongkees, L B., et al., "Electronystagmography", *Acta otolaryngologica*(Stockholm), Supplement 189, (1964),109 pgs.

Lysakowski, A , et al., "Physiological identification of morphologically distinct afferent classes innervating the cristae ampullares of the squirrel monkey", *Journal of Neurophysiology*, 73(3), (Mar. 1995),1270-81.

McClure, J A., et al., "Vestibular asymmetry. Some theoretical and practical considerations", *Archives of Otolaryngology*, 109(10), (Oct. 1983),682-7.

Minor, L B., et al., "Horizontal vestibulocular reflex evoked by high-acceleration rotations in the squirrel monkey. I. Normal responses", *Journal of Neurophysiology*, 82(3), (Sep. 1999),1254-70.

Minor, L B., et al., "Influence of static head position on the horizontal nystagmus evoked by caloric, rotational and optokinetic stimulation in the squirrel monkey", *Experimental Brain Research*, 82(1), (1990),1-13.

Minor, L B., et al., "Vestibular-nerve inputs to the vestibulo-ocular reflex: a functional-ablation study in the squirrel monkey", *Journal of Neuroscience*, 11(6), (Jun. 1991),1636-48.

Moore, S T., et al., "A geometric basis for measurement of three-dimensional eye position using image processing", *Vision Research*, 36(3), (Feb. 1996),445-59.

Moore, S T., et al., "VTM—an image-processing system for measuring ocular torsion", *Computer Methods & Programs in Biomedicine*, 35(3), (Jul. 1991),219-30.

O'Leary, D P., et al., "Analysis of vestibulo-ocular reflex using sweep frequency active head movements", *Advances in Oto-Rhino-Laryngology*, 41, (1988),179-83.

O'Leary, D P., "Test/retest reliability of the vestibular autorotation test in healthy subjects", *Otolaryngology—head and neck surgery : official journal of American Academy of Otolaryngology—Head and Neck Surgery*, 119(1), (Jul. 1998),147-8.

Paige, G D., "Nonlinearity and asymmetry in the human vestibulo-ocular reflex", *Acta Oto-Laryngologica*, 108(1-2), (Jul.-Aug. 1989),1-8.

Peterka, R J., et al., "Age-related changes in human vestibulo-ocular and optokinetic reflexes: pseudorandom rotation tests", *Journal of Vestibular Research*, 1(1), (1990-1991),61-71.

Peterka, R J., et al., "Age-related changes in human vestibulo-ocular reflexes: sinusoidal rotation and caloric tests", *Journal of Vestibular Research*, 1(1), (1990-91),49-59.

Peterka, R J., et al., "Calibration techniques for video oculography", *Journal of Vestibular Research*, 6, (1996),S75.

Rey, C G., et al., "Transient analysis of vestibular nystagmus", *Biological Cybernetics*, 69(5-6), (1993),395-405.

Robinson, D A., "A method of measuring eye movement using a scleral search", *IEEE Translations on Biomedical Electronics*, 10, (1963),137-145.

Robinson, D A., "The mechanics of human saccadic eye movement", *The Journal of Physiology*, (Nov. 1964),245-64.

Robinson, D A., "The use of matrices in analyzing the three-dimensional behavior of the vestibulo-ocular reflex", *Biological Cybernetics*, 46(1), (1982),53-66.

Saadat, D , et al., "Comparison of vestibular autorotation and caloric testing", *Otolaryngology—Head & Neck Surgery*, 113(3), (Sep. 1995),215-22.

SPSS, Inc., "SYSTAT 8.0 : statistics", Chicago, IL : *SPSS, Inc.*, (1998),363-366.

Stockwell, C W., "Interpretation and usefulness of rotational testing", *In:Handbook of balance function testing* / [edited by] Gary P. Jacobson, Craig W. Newman, Jack M. Kartush, San Diego, Calif. : Singular Pub. Group,(1997),249-258.

Tomlinson, R D., et al., "Analysis of human vestibulo-ocular reflex during active head movements", *Acta Oto-Laryngologica*, 90(3-4), (Sep.-Oct. 1980)184-90.

Wade, S W., et al., "Time constant of nystagmus slow-phase velocity to yaw-axis rotation as a function of the severity of unilateral caloric paresis", *American Journal of Otology*, 20(4), [erratum appears in Am J Otol Jan. 2000;21(1):153],(Jul. 1999),471-8.

Wilson, Victor J., et al., "Biophysics of the Peripheral End Organs (Ch.3) & Mechanoneural Transduction and the Primary Afferent Response (Ch.4)", *In: Mammalian Vestibular Physiology*, Plenum Press, New York, New York.,(1979),41-69 & 92-107.

Wolfe, J W., et al., "Low-frequency harmonic acceleration in the evaluation of patients with peripheral labyrinthine disorders", *In:Nystagmus and vertigo : clinical approaches to the patient with dizziness* / edited by Vicente Honrubia and Mary A.B. Brazier, New York : Academic Press,(1982),95-105.

* cited by examiner

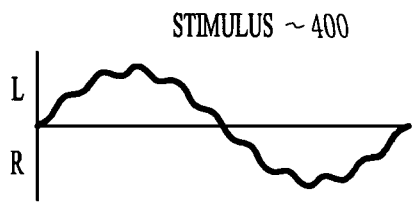
FIG. 4A
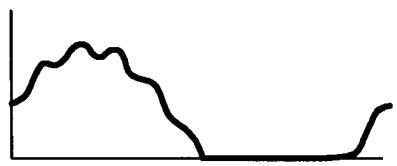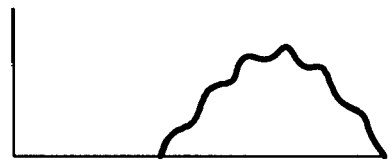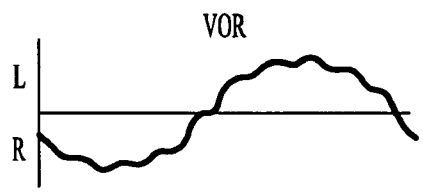
FIG. 4B
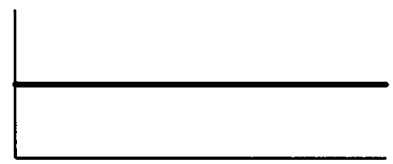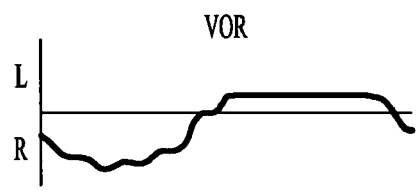
FIG. 4C

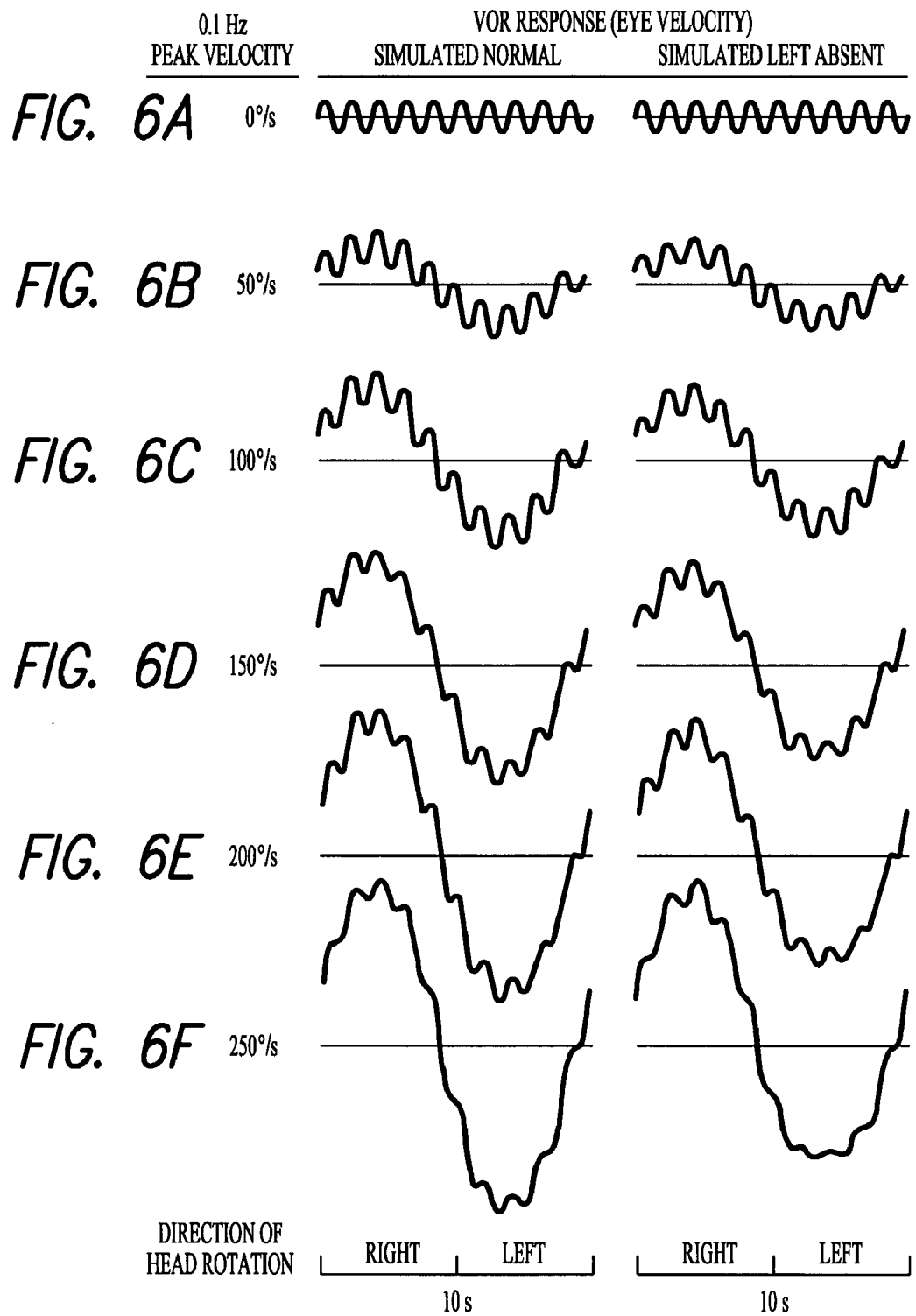

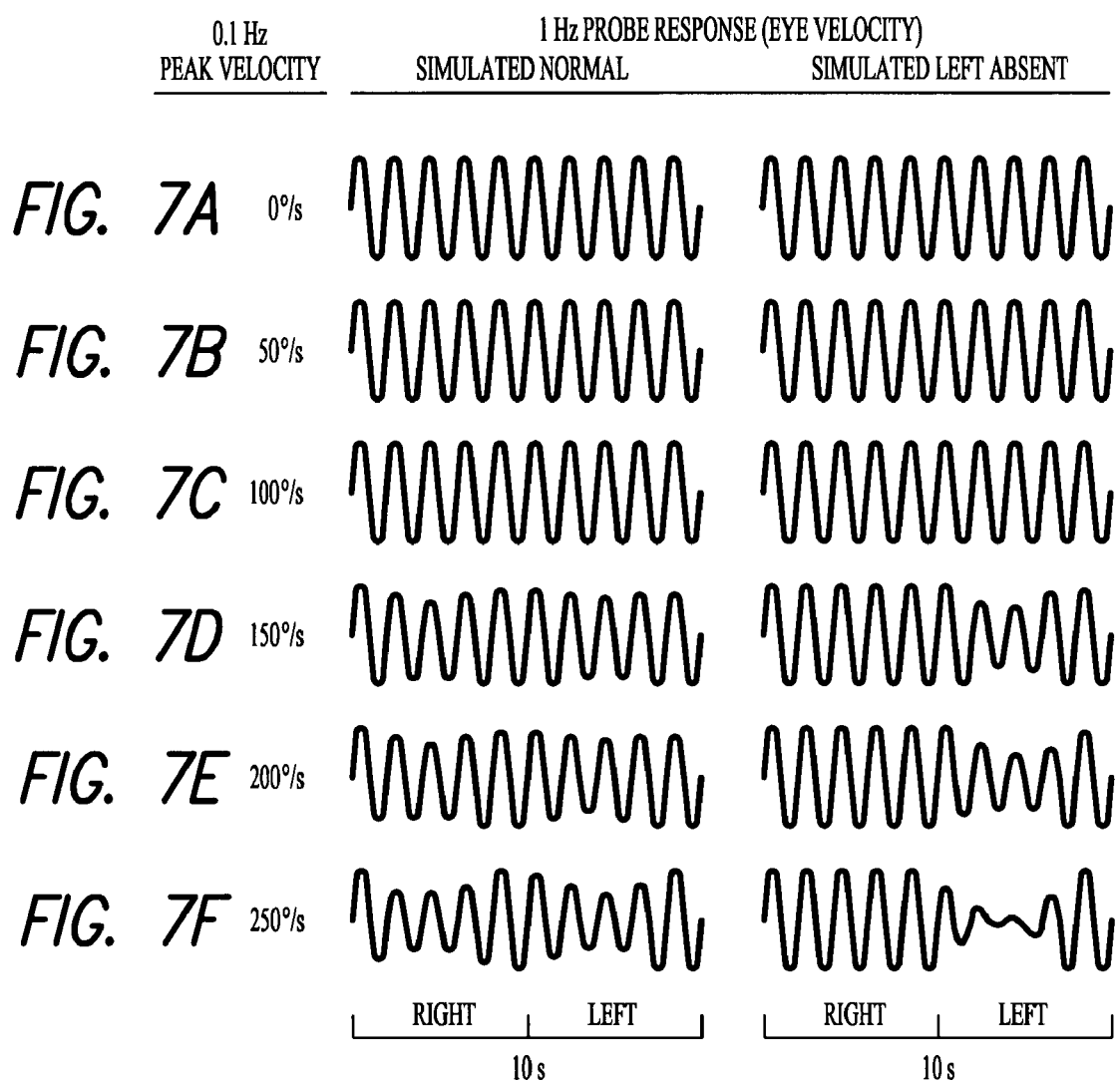

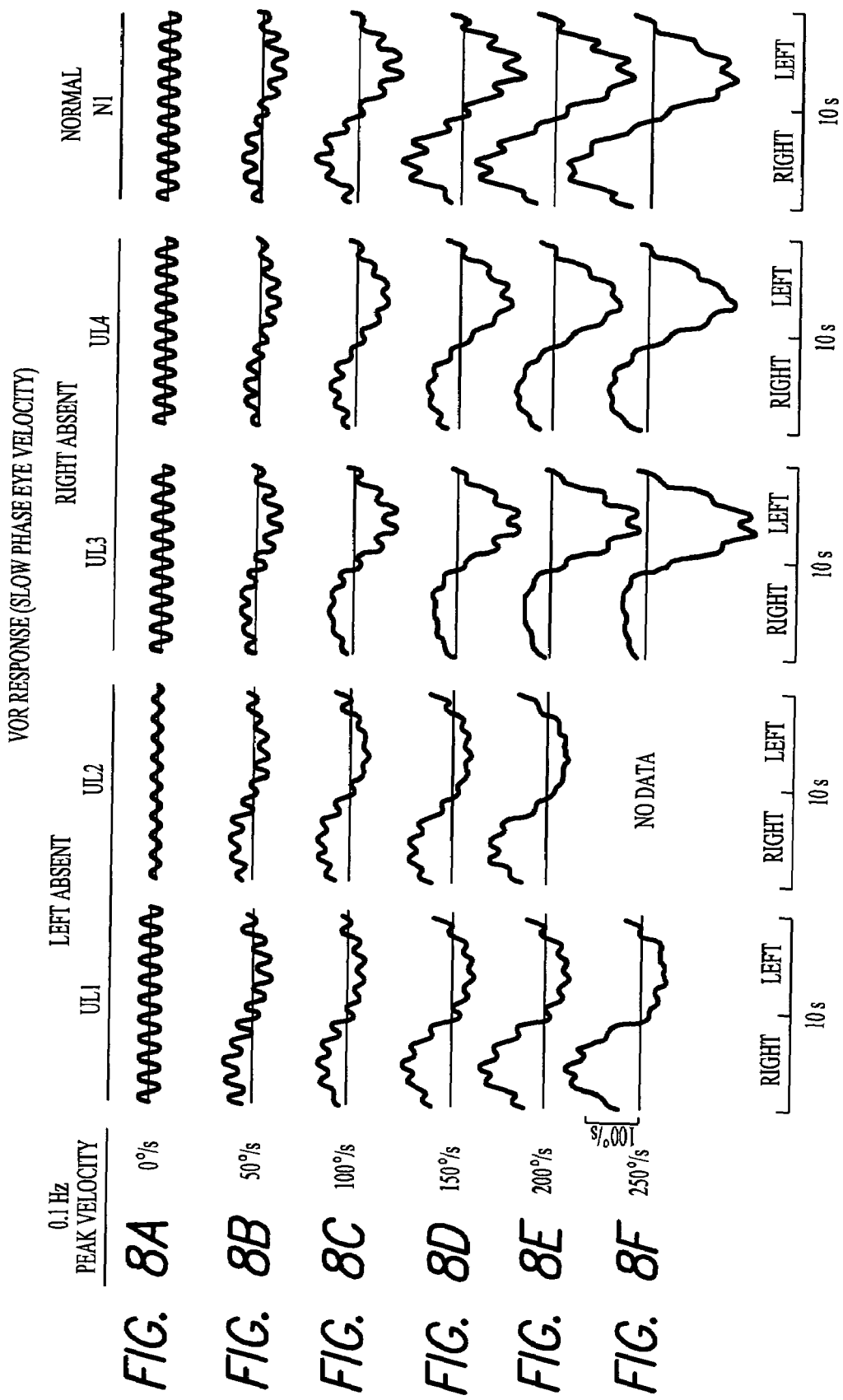

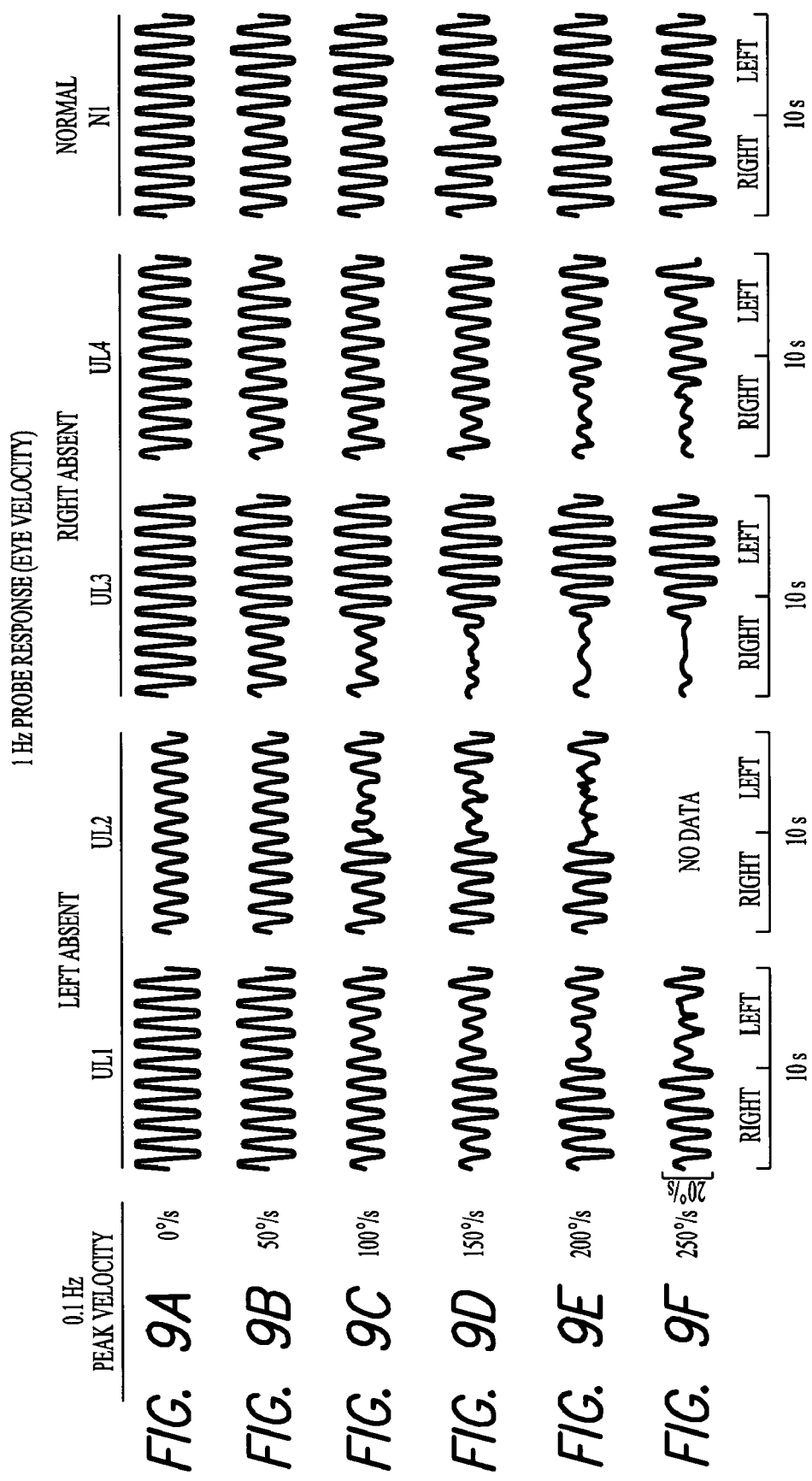

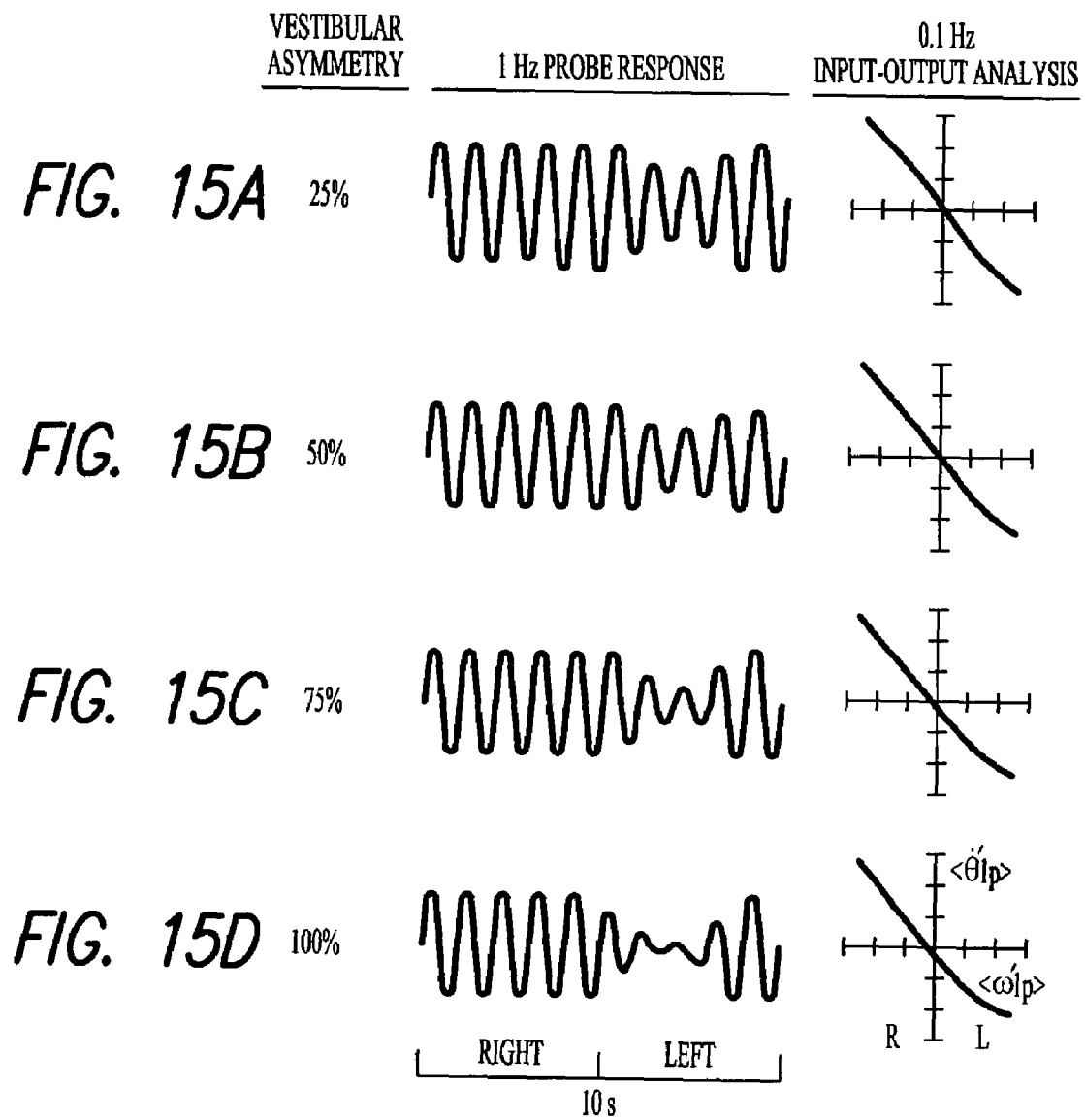

SINE COMPONENT MEASURES
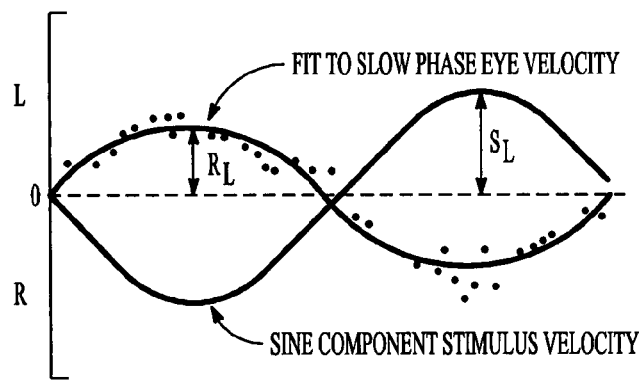
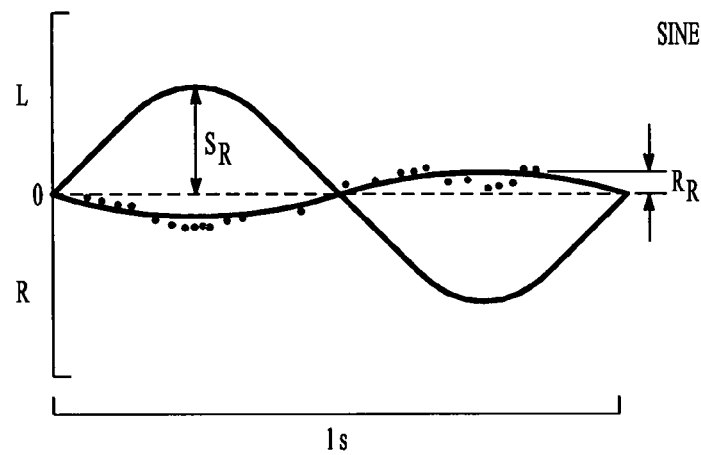
SINE COMPONENT GAIN DURING LEFTWARD STEP
$$VOR_L = \frac{R_L}{S_L}$$
SINE COMPONENT GAIN DURING RIGHTWARD STEP
$$VOR_R = \frac{R_R}{S_R}$$
SINE COMPONENT GAIN ASYMMETRY
$$= \frac{VOR_L - VOR_R}{VOR_L + VOR_R} \times 100$$
(+) SIGN = DECREASED RESPONSE TO RIGHTWARD ROTATION
(-) SIGN = DECREASED RESPONSE TO LEFTWARD ROTATION
FIG. 17B

BIAS-PROBE ROTATION TEST OF VESTIBULAR FUNCTION

RELATED APPLICATION

This application is a divisional of U.S. application Ser. No. 10/762,211, filed on Jan. 21, 2004, now U.S. Pat. No. 7,285,099 which claims priority under 35 U.S.C. 119(e) from U.S. Provisional Application Ser. No. 60/441,853 filed Jan. 21, 2003, which applications are incorporated herein by reference.

GOVERNMENT INTEREST STATEMENT

The invention arose from work under a contract with the National Institutes of Health, grant no. DC04592. The Government may have certain rights in the invention.

FIELD OF THE INVENTION

This invention relates generally to quantitative assessment of vestibular function, more particularly to methods and apparatus for medical evaluation of patients with balance and equilibrium complaints.

BACKGROUND OF THE INVENTION

The medical evaluation of patients with balance and equilibrium complaints often includes an assessment of their vestibular function. The goal of this assessment is to determine if peripheral vestibular function is normal or abnormal. If vestibular function is found to be abnormal, is one ear involved or are both ears affected? How severe is the abnormality? Is the abnormality stable or fluctuating? Standard clinical tests frequently do not provide adequate answers to one or all of these questions.

Conventional clinical rotation testing typically uses sinusoidal or velocity step motion with moderate stimulus amplitudes (50-100°/s peak velocity) to assess vestibular function by providing a natural rotational stimulus to the semicircular canals and measuring eye movements evoked by the vestibulo-ocular reflex (VOR). Conventional rotation testing has good test-retest reliability, but relatively low sensitivity. Testing sometimes fails to detect a vestibular abnormality or, if an abnormality is detected, to provide a detailed assessment of the severity and/or the side of lesion.

Quantitative assessment of vestibular function relies primarily on measurements of reflexive eye movements (i.e. the VOR) evoked by either natural or artificial stimulation of the vestibular receptors of the inner ear. Visual acuity is maintained during head movement by the generation of compensatory eye movements that maintain the direction of gaze fixed in space. In the light, the VOR, smooth pursuit, and optokinetic reflex systems work together to generate these compensatory eye movements. But in darkness, compensatory eye movements are generated only by the VOR. Therefore, measurements of VOR eye movements in the dark (or sometimes using high frequency head motions where visual reflexes are ineffective) provide an indirect means of assessing peripheral vestibular function.

There are four clinical tests of the vestibular system currently in use on a regular basis. They each have limitations in reliability, applicability, diagnostic precision, and costs that the new rotation test stimulus and analysis method overcome.

There are two main quantitative clinical tests based on VOR measures: caloric and rotation. Rotation testing includes both conventional passive rotations (sometimes referred to as slow harmonic acceleration or SHA testing) and active, subject initiated autorotation tests. More recently, the "head impulse test" or "Halmagyi head thrust" test has become popular as an easily applied qualitative method for detecting the existence of bilateral or unilateral vestibular dysfunction. These various tests, including their advantages and limitations, are described in more detail below.

Caloric test. The caloric test artificially stimulates the inner ear vestibular receptors using either warm-water or cold-water irrigations of the external ear canals. This evokes eye movements, which are measured and compared across ears to determine vestibular asymmetry. Patients are placed in a supine position with the head elevated about 30° in a darkened room. This head position places one set of vestibular receptors, the horizontal semicircular canals, into an earth-vertical orientation. An irrigation creates a thermal gradient across the inner ear that stimulates the horizontal canal, primarily by inducing a convective fluid movement within the distal loop of the canal, and secondarily, by direct thermal effects. This fluid movement stimulates receptor hair cells, which in turn modulate the activity of the $8^{th}$ nerve afferents that innervate the horizontal canal. A warm water irrigation results in an increased afferent discharge rate, and a cold water irrigation causes a decreased discharge rate. The increased discharge caused by warm irrigations evokes a sensation of sustained rotation toward the irrigated ear and evokes a compensatory VOR eye rotation away from the irrigated ear. Cold water irrigations evoke oppositely directed sensations and compensatory eye movements.

"Slow phase" compensatory eye movements are interspersed with "fast phase" eye movements that reset the eye position towards the straight ahead gaze position, producing a triangular-shaped eye position waveform referred to as vestibular-evoked "nystagmus." To quantify this response, the slow phase and fast phase components are separated from one another. The slow phase component is analyzed by calculating its slope which gives the slow phase eye velocity (units °/s) for each beat of nystagmus. The peak velocity is taken as a measure of the responsiveness of the ear to a particular irrigation.

A complete caloric test typically consists of measuring the peak velocity response to four separate irrigations (both warm and cold irrigations in each of the two ears). These four peak velocity measures are scored by the calculation of Jongkees' percentage measures of "reduced vestibular response" (RVR), sometimes referred to as canal paresis, and "directional preponderance" (DP) (See reference 35 listed below). If responses are significantly different in the two ears (typically RVR greater than 25% difference), the ear with the lower response is typically considered to be abnormal. If all four irrigations produce below normal or absent responses, this implies that the patient may have bilaterally reduced or absent vestibular function. The DP measure compares the responses of irrigations that produce right-beating nystagmus with those that produce left-beating nystagmus. If DP is abnormal (typically greater than 25%), this suggests that some non-specific uncompensated imbalance of vestibular function is present.

The chief advantage of the caloric test is that each ear is stimulated individually. This allows for the identification of reduced vestibular function in an ear even though the patient might be well compensated for the lesion and may not express any other overt signs of an acute vestibular lesion. In addition, the RVR and DP measures are quantitative in nature and can be used to grade the severity of the vestibular asymmetry.

Caloric testing has several significant limitations. The thermal stimulus that reaches the inner ear depends upon many anatomical factors (i.e., temporal bone thickness, dimensions of middle ear space, fluid in the middle ear space, variation in blood flow) and procedural factors such as the technician's skill. As a result, there is high variability across subjects in delivery of the thermal stimulus to the inner ear, due to differences in temporal bone thickness dimensions of middle ear space, fluid in the middle ear space, and variations in blood flow. These factors make it difficult to detect small differences in responses between both ears. The end result is that test-retest reliability is poor, making the test a poor choice (unsuitable) for tracking changes in vestibular function over time. In addition, response variability limits the detection of small differences in responses between the two ears. The identification of bilateral vestibular loss is also uncertain due to the wide variations in response amplitudes in a normal population. Finally, the unusual nature of the stimulus (evoking sensations of a long duration rotational motion in a supine position that conflicts with gravity cues from the otolith organs of the inner ear) often provokes nausea in subjects (poor tolerance by subjects) susceptible to motion sickness.

Conventional Rotation Test. The conventional rotation test involves a patient being rotated upright in a clinical rotation chair in a completely dark room. The chair is rotated about an earth-vertical axis, with rotations of moderate amplitude (50-100°/s peak velocity). The typical rotations are sinusoidal, with frequencies ranging from 0.01 to 1.0 Hz. Rotational velocity step stimuli and sometimes pseudorandom or sum-of-sines stimuli are also used.

Rotation testing differs from caloric testing in that a natural rotational stimulus, which stimulates both ears simultaneously, is used to evoke compensatory VOR eye movements. Patients are tested in a completely dark room to eliminate visually generated eye movements. During testing, they are seated upright in a chair mounted on a servo-controlled motor. The motor delivers accurately controlled rotational motions of the chair about an earth-vertical axis. This motion stimulates primarily the horizontal semicircular canals in both ears. In a subject with normal vestibular function, a rotation towards the right causes an increased neural discharge rate in $8^{th}$ nerve afferents innervating the right side horizontal canal, and a decreased discharge rate in afferents innervating the left horizontal canal. The opposite occurs for rotations to the left. The central nervous system (CNS) uses this "push-pull" neural activity in the two ears to generate VOR eye movements in a direction opposite to the head rotation.

Conventional rotation testing uses rotations with moderate amplitudes (50-100°/s peak velocity). The motion profiles typically are sinusoidal with frequencies ranging from 0.01 to 1.0 Hz [54,59]. Rotational velocity step stimuli [5,32], and sometimes pseudorandom or sum-of-sines stimuli are also utilized [10,47]. Rotation-evoked nystagmus is analyzed in a manner similar to caloric-evoked nystagmus. The nystagmus is separated into slow and fast phase components. The slope of the compensatory slow phase component provides a measure of the slow phase eye velocity over time. With sinusoidal stimulation, this slow phase eye velocity component is sinusoidally modulated at the stimulus frequency. A sinusoidal curve fit to the eye velocity gives quantitative measures of the VOR response that include: VOR gain (response amplitude divided by stimulus amplitude), VOR phase (timing of the response relative to the stimulus), VOR bias (average value of slow phase eye velocity over a complete stimulus cycle), and VOR gain asymmetry (comparison of VOR gain during rotation to the right versus rotation to the left). These response parameters vary as a function of the stimulus frequency, and deviations from the normal pattern are indicative of different types of vestibular dysfunction. For example, normal VOR gain with abnormal phase advance at lower test frequencies, and normal response symmetry is associated with a well compensated unilateral vestibular loss. Reduced VOR gain with abnormal phase advance and normal symmetry indicates a bilateral vestibular loss with the reduction in gain related to the severity of the bilateral loss.

The natural stimulus used by rotation testing, and the precise means available for delivering the rotational stimulus, provide several advantages over caloric testing. First, the test-retest reliability of rotation testing is good, making rotation testing amenable to tracking function over time. Second, the rotation test VOR gain measure has a limited range of normal values, making rotation testing particularly useful in assessing bilateral loss of vestibular function. Third, for sinusoidal rotation tests, the repetitive nature of the stimulus affords great opportunity to use averaging to improve test reliability and the possibility to obtain useful results from partially corrupted data records. Fourth, rotation testing is well tolerated by nearly all patients and only rarely evokes nausea.

The chief disadvantage of rotation testing is that it often does not provide reliable information (inability to provide reliable information) about which ear is abnormal in a patient with unilateral vestibular dysfunction. There are two main reasons for this failure. First, animal studies indicate that the $8^{th}$ nerve vestibular afferents have a high resting discharge rate averaging about 90 impulses/s. Therefore, for the moderate stimulus amplitudes used in conventional rotation testing, each ear is able to accurately encode bidirectional head rotations without driving the discharge rate of a significant number of neurons to zero during any portion of the sinusoidal stimulus cycle. That is, even if vestibular function is completely absent in one ear, the other ear is able to accurately encode bidirectional head movements, and the CNS is therefore able to generate an accurate VOR. Second, the CNS is able to compensate for the acute effects of a unilateral loss of vestibular function which might otherwise be used to identify the existence of a unilateral vestibular deficit. Specifically, an acute loss of vestibular function results in a strong "spontaneous nystagmus." This nystagmus occurs because the CNS normally compares the neural activity in the two ears and generates compensatory eye movements proportional to the difference in activity between the two ears. This spontaneous nystagmus typically diminishes over a time course of several days as the CNS rebalances the central VOR neural mechanisms. Once this rebalancing is achieved, only minor signs of vestibular dysfunction remain in the results of conventional rotation tests (specifically, low frequency phase advance, and occasionally, gain asymmetries), and even these minor signs have not been found to reliably indicate the side of the lesion.

A second important limitation in rotation testing is its poor sensitivity in detecting a compensated partial unilateral vestibular loss (inability to reliably identify any abnormality in patients who have only a partial loss of vestibular function). A recent study demonstrated that VOR gain measures from rotation tests using both velocity step and sum-of-sines stimuli were uncorrelated with the severity of unilateral vestibular dysfunction as characterized by the caloric RVR measure (See reference 57 listed below). The mean VOR time constant, determined from velocity step responses and indirectly from responses to sum-of-sines stimuli, did show a consistent decline with increasing caloric RVR. However, the wide variability of results indicate that many patients with a 40-60% caloric RVR, and some with a 60-80% RVR, would not be distinguished from a normal population using conventional rotation testing. In addition, neither of these rotation tests provided a reliable indication of the side of vestibular loss, except in the 80-100% RVR patient group where velocity step rotations showed a small asymmetry between VOR time constants determined during rotations toward and away from the absent side.

A third limitation of conventional rotation testing is the ambiguity between rotation test results in patients with a partial bilateral loss and a compensated unilateral loss (inability to distinguish between patients with a partial bilateral vestibular loss and a compensated unilateral vestibular loss of function). Both abnormalities produce a reduction in the VOR time constant and, equivalently, a low frequency phase advance. A partial bilateral vestibular loss may cause only a mild reduction in VOR gain such that the VOR gain may remain within the normal range while the VOR time constant is reduced. This pattern of normal gain and reduced time constant is indistinguishable from a compensated unilateral vestibular loss pattern.

Autorotation Test. In the autorotation test, the patient rotates the head side-to-side in synchrony with an audio tone cue while viewing a fixed visual target. The autorotation test evaluates the VOR at higher frequencies of head rotation (2-6 Hz) than those in conventional rotation tests. Testing has become standardized using commercially available systems. Tests are performed in the light with the subject instructed to gaze at a fixed visual target. An audio tone cues the test subject to oscillate his/her head in time with the tone. The tone cue begins at 0.5 Hz and continuously increases to 6 Hz in about 20 s. Head movements at lower frequencies are used to calibrate the eye movement recordings, and higher frequency VOR responses are quantified using spectral analysis techniques to calculate response gain and phase at frequencies of 2 to 6 Hz. Deviations of gain and phase responses from normal ranges are indicative of abnormal vestibular function.

Autorotation tests evaluate the VOR in a frequency range higher than either caloric or conventional rotation tests. Since VOR function in this higher frequency range is important for maintenance of clear vision during head movements, autorotation testing provides physiologically relevant information related to gaze stability. The equipment for this test is inexpensive and portable, particularly compared to conventional rotation testing. There have been claims that this test has high sensitivity, with some patients showing abnormalities on autorotation tests even though caloric results were normal.

Although this test has been in use for over 10 years, there is little consensus regarding its utility and reliability. A recent study (See reference 27 listed below) investigated autorotation test reliability in 12 normal subjects and concluded that "Unfortunately, the test-retest reliability of the VAT [vestibular autorotation test] is poor, and therefore it cannot be used routinely." This result, however, was disputed by the originator of the VAT system (See reference 44 listed below). Potential factors contributing to poor reliability include: eye movement recording artifacts caused by rapid head movements (high head accelerations), imperfect measurements of head movements (imperfect monitoring of head motion) that produce inaccurate evaluations of vestibular function, inconsistent ability of subjects to achieve regular oscillations at higher frequencies, and analysis artifacts introduced by fast phase eye movements. Finally, the scientific literature on autorotation has focused on the detection of abnormal responses, but little information (little research) is available about the test's ability to localize vestibular dysfunction to one or both ears and to quantify the magnitude of the deficit.

Head impulse test. In the head impulse test, an examiner rotates a patient's head with a rapid, high acceleration rotation though an angle of about 20-30° while the patient attempts to maintain higher gaze on a fixed target. The examiner looks for corrective eye movements following the head rotation, indicating that vestibular function is deficient and unable to generate VOR eye movements that fully compensate for the head rotation. Typically, the rotation is about the head's vertical axis which stimulates primarily the horizontal canals. The patient attempts to maintain his/her gaze fixed on a target during this maneuver. In patients with severe canal paresis, the rotation towards the dysfunctional ear or ears produces an inadequate compensatory VOR. This inadequate VOR causes the eyes to move off target, with the result being that a visually guided corrective saccade is generated to reacquire the target at the conclusion of the head rotation. The presence of this corrective saccade is a convenient qualitative clinical sign indicating abnormal canal function. Alternatively, if eye movements are recorded during head rotations, the gain of the VOR can be calculated and used as an indicator of VOR function.

The main advantage of head impulse testing is that the qualitative version of the test (i.e. using the presence of a corrective saccade as a sign of abnormality) can be performed by a knowledgeable practitioner with no equipment. In cases where patients were known to have a complete unilateral loss of vestibular function, the test has been shown to have 100% sensitivity and specificity. In addition, recent research indicates that this technique can be extended to include head rotations about oblique axes that allow for evaluation of the vertical semicircular canals.

The chief disadvantage of head impulse testing is that it has recently been shown in a study to have poor sensitivity in cases of less severe canal paresis (See reference 7 listed below). This blinded study compared the results of conventional caloric testing with head impulse testing. In patients with severe canal paresis (75-100% RVR on caloric testing), head impulse testing showed abnormal results in 77% of these patients. However, head impulse testing revealed abnormalities in only 9.5% of patients with moderate paresis (50-75% RVR) and 0% of patients with mild paresis (25-50% RVR). Overall, it was concluded that head impulse testing was useful in detecting severe paresis, but could not serve as a replacement for the caloric test. Major limitations are that: (1) it doe not adequately identify mild-to-moderate vestibular dysfunction in a single ear, and (2) the test cannot be used in patients with any limitations in neck mobility (e.g. limitations due to whiplash, arthritis).

Perhaps the sensitivity of head impulse testing could be improved by the use of controlled rotations and accurate eye movement recordings that have been applied in research studies. However, clinical application of these improved techniques is problematic for two reasons. First, better control of rotations would probably require whole body rotations. A rotation device to accomplish this would need high torques to generate the high accelerations required for these tests. Rotation devices that are currently in most clinical vestibular laboratories do not have adequate torque. Second, the short duration of the head impulse requires an accurate method of recording eye movements at a high sampling rate. Currently, the search coil technique seems to be the only adequate technology available. However, search coils are inconvenient to apply in a clinical setting, have some risk associated with their use (i.e. corneal injury), and can only be used for short time periods.

Finally, patients with neck injury or other limitations in neck mobility cannot be tested using rapid head on body rotations. Patients in this category would include patients with balance complaints associated with accidents causing whiplash injuries, and elderly patients with limited mobility due to arthritic conditions.

REFERENCES

The following references provide additional background with respect to vestibular functions, related material, and the testing thereof:

1. Aw, S. T., Halmagyi, G. M., Haslwanter, T., Curthoys, I. S., Yavor, R. A., Todd, M. J. (1996) Three-dimensional vector analysis of the human vestibuloocular reflex in response to high-acceleration head rotations. II: Responses in subjects with unilateral vestibular loss and selective semicircular canal occlusion. J Neurophysiol 76:4021-4030

2. Aw, S. T., Halmagyi, G. M., Black, R. A., Curthoys, I. S., Yavor, R. A., Todd, M. J. (1999) Head impulses reveal loss of individual semicircular canal function. J Vest Res 9:173-180

3. Baloh, R. W., Honrubia, V. (1990) Clinical Neurophysiology of the Vestibular System. F A Davis, Philadelphia 4. Baloh, R. W., Honrubia, V., Yee, R. D., Hess, K. (1984) Changes in the human vestibulo-ocular reflex after loss of peripheral sensitivity. Ann Neurol 16:222-228

5. Baloh, R. W., Sills, A. W., Honrubia, V. (1979) Impulsive and sinusoidal rotatory testing: A comparison with results of caloric testing. Laryngoscope 89:646-654

6. Benson, A. J. (1984) Motion Sickness. In: Dix M R, Hood J D (eds) Vertigo. John Wiley & Sons, Chichester, pp 391-426

7. Benyon, G. J., Jani P., Baguley, D. M. (1998) A clinical evaluation of head impulse testing. Clin Otolaryngol 23:117-122

8. Black, F. O., Shupert, C. L., Peterka, R. J. et al. (1989) Effects of unilateral loss of vestibular function on the vestibulo-ocular reflex and postural control. Ann Otol Rhinol Laryngol 98:884-9

9. Blanks, R. H. I., Curthoys, I. S., Markham, C. H. (1975) Planar relationships of the semicircular canals in man. Acta Otolaryngol (Stockh) 80:185-196

10. Bouveresse, A., Kalfane, K., Gentine, A., Eichhorn, J. L., Kopp, C. (1998) Pseudorandom rotational stimuli of the vestibulo-ocular reflex in humans: normal values of the transfer function. Acta Otorhinolaryngologica (Belg) 52:207-214

11. Clarke, A. H., Teiwes, W., Scherer, H. (1991) Video-oculography—an alternative method for measurement of three-dimensional eye movements. In: Schmid, R., Zambarbieri, D. (eds) Oculomotor Control and Cognitive Processes. Elsevier Science Publishers B. V., North-Holland, pp 431-443

12. Cleveland, W. S. (1979) Robust locally weighted regression and smoothing scatterplots. J Am Atat Assoc 74:829-836

13. Crane, B. T., Demer, J. L. (1998) Human horizontal vestibulo-ocular reflex initiation: effects of acceleration, target distance, and unilateral deafferentation. J Neurophysiol 80:1151-1166

14. Curthoys, I. S., Halmagyi, G. M. (1995) Vestibular compensation: a review of the oculomotor, neural and clinical consequences of unilateral vestibular loss. J Vestib Res 5:67-107

15. Curthoys, I. S., Blanks, R. H. I., Markham, C. H. (1977) Semicircular canal functional anatomy in cat, guinea pig and man. J Morphol 151:17-34

16. Fernandez, D., Goldberg, J. M. (1971) Physiology of peripheral neurons innervating semicircular canals of the squirrel monkey. II: Response to sinusoidal stimulation and dynamics of peripheral vestibular system. J Neurophysiol 34:661-675

17. Fetter, M., Zee, D. S., (1988) Recovery from unilateral labyrinthectomy in rhesus monkey. J Neurophysiol 359:370-393

18. Foster, C. A., Foster, B. D., Spindler, J., Harris, J. P. (1994) Functional loss of the horizontal doll's eye reflex following unilateral vestibular lesions. Laryngoscope 104:473-478

19. Furman, J. M., Cass, S. P. (1996) Laboratory evaluation. I: Electronystagmography and rotational testing. In: Baloh, R. W., Halmagyi, G. M. (eds) Disorders of the Vestibular System. Oxford University Press, New York, pp 191-210

20. Furman, J. M., Goebel, J. A., Hanson, J., Schumann, T. and Interlaboratory Rotational Chair Study Group: Hamid, M. A., Honrubia, V., Peterka, R. J., Shephard, N. T., Stockwell, C. W., Wall III, C. (1999) Interlaboratory variability of rotational chair test results II: Analysis of simulated data. Otolaryngol Head Neck Surg (in press)

21. Galiana, H. L. (1991) A nystagmus strategy to linearize the vestibulo-ocular reflex. IEEE Tran Biomed Eng 38:532-543

22. Galiana, J. L., Flohr, H., Melvill Jones, G. (1984) A reevaluation of intervestibular nuclear coupling: Its role in vestibular compensation. J Neurophysiol 51:242-259

23. Galiana, H. L., Outerbridge, J. S. (1984) A bilateral model for central neural pathways in vestibuloocular reflex. J Neurophysiol 51:210-241

24. Goldberg, J. M., Fernandez, D. (1971) Physiology of peripheral neurons innervating semicircular canals of the squirrel monkey. I: Resting discharge and response to constant angular accelerations. J Neurophysiol 34:635-660

25. Goldberg, J. M., Fernandez, D. (1971) Physiology of peripheral neurons innervating semicircular canals of the squirrel monkey. III: Variations among units in their discharge properties. J Neurophysiol 34:676-684

26. Graybiel A., Wood, S. D., Miller, E. F., Cramer, D. B. (1968) Diagnostic criteria for grading the severity of acute motion sickness. Aerospace Med 39:453-455

27. Guyot, J. P., Psillas, G. (1997) Test-retest reliability of vestibular autorotation testing in healthy subjects. Otolaryngol Head Neck Surg 117:704-707

28. Halmagyi, G. M., Curthoys, I. S. (1988) A clinical sign of canal paresis. Arch Neurol 45:737-739

29. Haslwanter, T. (1995) Mathematics of three-dimensional eye rotations. Vision Res 35:1727-39

30. Hatamian, M., Anderson, D. J., (1983) Design considerations for a real-time ocular counterroll instrument. IEEE Trans Biomed Eng BME 30:278-28831.

31. Henry, D. F., Dibartolomeo, J. D. (1993) Closed-loop caloric, harmonic acceleration and active head rotation tests: Norms and reliability. Otolaryngol Head Neck Surg 109:975-98732.

32. Honrubia, V., Jenkins, H. A., Baloh, R. W., Yee, R. D., Lau, C. G. Y. (1984) Vestibulo-ocular reflexes in peripheral labyrinthine lesions: I. Unilateral dysfunction. Am J Otolaryngol 5:15-26

33. Honrubia, V., Marco, J., Andrews, J., Minser, K., Yee, R. D., Baloh, R. W. (1985) Vestibulo-ocular reflexes in peripheral labyrinthine lesions: III. Bilateral dysfunction. Am J Otolaryngol 6:342-352

34. Jenkins, H. A., Honrubia, V., Baloh, R. W. (1982) Evaluation of multiple-frequency rotatory testing in patients with peripheral labyrinthine weakness. Am J Otolaryngol 3:182-188

35. Jongkees, L. B. W., Philipszoon, A. J. (1964) Electronystagmography. Acta Otolarynogol (Stockh) Suppl 189

36. Lysakowski, A., Minor, L. B., Fernandez, C., Goldberg, J. M. (1995) Physiological identification of morphologically distinct afferent classes innervating the cristae ampulares of the squirrel monkey. J. Neurophysiol 73:1270-1281

37. McClure, J. A., Lycett, P. (1983) Vestibular asymmetry. Arch Otolaryngol 109:682-687

38. Minor, L. B., Goldberg, J. M. (1990) Influence of static head position on the horizontal nystagmus evoked by caloric, rotational, and optokinetic stimulation in the squirrel monkey. Exp Brain Res 82:1-13

39. Minor, L. B., Goldberg, J. M. (1991) Vestibular-nerve inputs to the vestibulo-ocular reflex: A functional-ablation study in the squirrel monkey. J. Neurosci 111:1636-164840.

40. Minor, L. B., Lasker, D. M., Backous, D. D., Hullar, T. E. (1999) Horizontal vestibuloocular reflex evoked by high-acceleration rotations in the squirrel monkey. I. Normal responses. J Neuorphysiol 82:1254-1270

41. Moore, S. T., Curthoys, I. S., McCoy, S. G. (1991) VTM-An image-processing system for measuring ocular torsion. Computer Methods and Programs in Biomedicine 35:219-230

42. Moore, S. T., Haslwanter, T., Curthoys, I. S., Smith, S. T. (1996) A geometric basis for measurement of three-dimensional eye position using image processing. Vision Res 36:445-459

43. O'Leary, D. P., Davis, L. L., Kitsigianis, G. (1988) Analysis of vestibulo-ocular reflex using sweep frequency active head movements. Adv Otorhinolaryngol 4:179-183

44. O'Leary, D. P. (July 1998) Letters to editor in response to: Test-retest reliability of vestibular autorotation testing in healthy subjects. pp. 147-148

45. Paige, G. D. (1989) Nonlinearity and asymmetry in the human vestibulo-ocular reflex. Acta Otolaryngol (Stockh) 108:1-8

46. Peterka, R. J., Black, F. O., Schoenhoff, M. B. (1990) Age-related changes in human vestibulo-ocular reflexes: Sinusoidal rotation and caloric tests. J Vest Res 1:49-59

47. Peterka, R. J., Black, F. O., Schoenhoff, M. B. (1990) Age-related changes in human vestibulo-ocular and optokinetic reflexes: Pseudorandom rotation tests. J Vest Res 1:61-71

48. Peterka, R. J., Merfeld, D. M. (1996) Calibration techniques for video-oculography. J Vest Res 6:S75

49. Rey, C. G., Galiana, H. L. (1993) Transient analysis of vestibular nystagmus. Biol Cybem 69:395-405

50. Robinson, D. A. (1963) A method of measuring eye movement using a scleral search coil in a magnetic field. IEEE Trans Biomed Elect 10:137-145

51. Robinson, D. A. (1964) The mechanics of human saccadic eye movement. J. Physiol (Lond) 174:245-264

52. Robinson, D. A. (1982) The use of matrices in analyzing the three-dimensional behavior of the vestibulo-ocular reflex. Biol Cybern 46:53-66

53. Saadat, D., O'Leary, D. P., Pulic, J. L., Kitano, H. (1995) Comparison of vestibular autorotation and caloric testing. Otolaryngol Head Neck Surg 113:215-222

54. Stockwell, C. W., Bojrab D. I. (1993) Interpretation and usefulness of rotational testing. In: Jacobson, G. P., Newman, C. W., Kartusy, J. M. (eds) Handbook of Balance Function Testing. Mosby Year Book, St. Louis, pp 249-258

55. Systat 8.0 Statistics (1998) SPSS Inc, Chicago, Ill. pp 363-366

56. Tomlinson, R. D., Saunders, G. E., Schwartz, D. W. F. (1980) Analysis of human vestibulo-ocular reflex during active head movements. Acta Otolaryngol (Stockh) 90:184-190

57. Wade, S. W., Halmagyi, G. M., Black, F. O., McGarvie, L. A. (1999) Time constant of nystagmus slow-phase velocity to yaw-axis rotation as a function of the severity of unilateral caloric paresis. Am J Otology 20:471-478

58. Wilson, V. J., Melvill Jones, G. (1979) Mammilian Vestibular Physiology. Plenum Press, New York 59. Wolfe, J. W., Engelken, E. J., Olson, J. E. (1982) Low-frequency harmonic acceleration in the evaluation of patients with peripheral labyrinthine disorders. In: Honrubia, V., Brazier, M. A. B. (eds) Nystagmus and vertigo: Clinical approaches to the patient with dizziness. Academic Press, New York, pp 95-105

All publications listed above are incorporated by reference herein, as though individually incorporated by reference.

BRIEF DESCRIPTION OF THE DRAWINGS

Embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in these embodiments and their equivalents.

FIG. 4A illustrates an embodiment of a 2-sine stimulus waveform, in accordance with the teachings of the present invention.

FIG. 4B illustrates an embodiment of a schematic response the 2-sine stimulus waveform of FIG. 4A in a normal subject, in accordance with the teachings of the present invention.

FIG. 4C illustrates an embodiment of a schematic response the 2-sine stimulus waveform of FIG. 4A in a right side unilateral loss subject, in accordance with the teachings of the present invention.

FIGS. 6A-6F show the simulated VOR output (simulated VOR slow phase eye velocity response to a 2-sine stimulus in normal and left unilateral loss subjects) for the simulation of FIG. 5, in accordance with the teachings of the present invention.

FIGS. 7A-7E show the portion of the simulated VOR eye velocity related to the high frequency probe component of a 2-sine rotational stimulus for the embodiment of the simulation of FIG. 5, in accordance with the teachings of the present invention.

FIGS. 8A-8F show a VOR slow phase horizontal eye velocity data recorded from one representative normal subject and four unilateral vestibular loss subjects in an embodiment using a 2-sine stimulus, in accordance with the teachings of the present invention.

FIGS. 9A-9F show a modulation of a VOR response to the probe component with the VOR slow phase velocity data filtered using a 0.5 to 5 Hz bandpass filter from the one representative normal subject and the four unilateral vestibular loss subjects of FIGS. 8A-8F in an embodiment using a 2-sine stimulus, in accordance with the teachings of the present invention.

FIGS. 15A-15D show the results of simulation analyses using embodiments for the probe analysis and input-output analysis procedures of FIGS. 10A and 12, in accordance with the teachings of the present invention.

FIG. 17B shows an embodiment for sine component measures for a test using PSS rotational stimulus, in accordance with the teachings of the present invention.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense.

In various embodiments, methods and apparatus for new rotation test stimulus and analysis methods overcome many of the limitations of conventional clinical tests of peripheral vestibular function, such as the four clinical tests described above. These embodiments provide a set of clinical tests that aid in the diagnosis of patients exhibiting symptoms of dizziness and balance instability, by determining whether inner ear (vestibular) asymmetries exist and, if so, identifying which ear is involved and the severity of the asymmetry. Embodiments of these methods and apparatus provide for new testing that delivers precise, repeatable stimuli to the vestibular system, can identify the existence of asymmetric vestibular function even in well compensated subjects, can identify which ear is dysfunctional, is well tolerated by most test subjects, can be performed in patients with limited neck mobility, and does not require active participation by the test subject.

Embodiments include a set of test stimuli and associated analysis methods that can be used to characterize an asymmetry of inner ear (vestibular) balance function. Various embodiments are based on an underlying principle that vestibular responses in one ear can be turned off, to allow responses in the other ear to be evaluated. In an embodiment, this is accomplished using a novel 2-component stimulus that is designed to control the motion of a conventional clinical rotation chair (a device that rotates a seated patient about a vertical axis).

Figure 1:
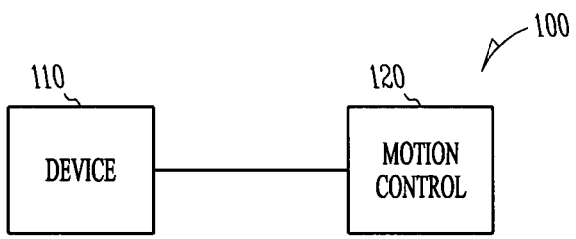
FIG. 1 depicts a block diagram of an embodiment for a system having a device to rotate a subject to be tested and a motion control to control the motion of the device, in accordance with the teachings of the present invention.

FIG. 1 depicts a block diagram of an embodiment for a system 100 having a device 110 to rotate a subject to be tested and a motion control 120 to control the motion of the device 110. In this embodiment, stimuli are provided to device 110 to turn off vestibular responses in one ear of the subject, while allowing vestibular responses in the other ear to be evaluated. In an embodiment, device 110 is a clinical rotation chair. In an embodiment, device 110 and motion control 120 are integrated. In an embodiment, system 100 is a clinical rotation chair. In an embodiment, rotation of device is about an earth-vertical axis with a subject's head oriented 20° nose down from Reid's plane to place the horizontal canal plane perpendicular to the axis of rotation. Medical centers and clinics that specialize in diagnosing balance disorders usually have conventional clinical rotation chair systems. Several medical equipment companies manufacture these systems. Embodiments for the rotation test and analysis may be incorporated into these existing systems by modifying the software that controls the movement of the chair in which the patient, subject, is seated and analyzes the evoked eye movements. In most cases, modifications to the existing rotation chair equipment (motors, eye movement recording equipment) would be minimal. In an embodiment, the novel rotation test and analysis may be incorporated into the clinical rotation chair systems at the time of manufacture, at a nominal cost, since the expense would not involve any new equipment but rather the novel programming of the rotation chair systems to include the new stimulus and analysis.

In various embodiments, tests are performed with the subject seated either in a completely dark room, or in an otherwise dark room except for a small illumined visual target on which the subject visually fixates and that rotates with the subject. For tests in the dark, rotational motion stimulates the vestibular motion sensors in the inner ear, and information from these motion sensors is used by the central nervous system to generate eye movements though a reflex known as the vestibulo-ocular reflex (VOR). For tests with the fixation light, visual information is used by the central nervous system to partially suppress the VOR eye movements evoked by the rotational stimulus. For both of these tests, eye movements are recorded and analyze, to obtain measures that characterize the symmetry of responses to rightward-and leftward-directed rotational motions. A significant asymmetry of these responses indicates that vestibular function is not equal in the two ears, and they also provide information about which ear is deficient and the extent of the deficiency.

An embodiment includes a first type of rotational stimuli applied to the rotational motion for testing. Another embodiment includes a second type of rotational stimuli applied to the rotational motion for testing. Each type concludes two separate components referred to as the "bias" and "probe" components. The bias component waveform has a high-amplitude and long duration rotational motion, while the probe component has a low-amplitude and high-frequency motion. The bias component for rotational motion is designed to temporarily turn off vestibular responses in one ear while the responsiveness in the opposite ear is simultaneously evaluated using the probe component of the stimulus. For example, rotational motion toward the right excites activity in the horizontal semicircular canal of the right ear (the vestibular motion sensor most affected by rotation when the head is in an upright position). This rotational motion toward the right inhibits activity in the left ear's horizontal semicircular canal. The bias component amplitude is designed to be large enough to completely inhibit the activity in the left horizontal canal during a portion of the rightward motion of the chair. When the left-side activity is completely inhibited, the left side motion receptor is unable to encode information related to the probe component motion. If the right side horizontal canal function is normal, the probe component motion is encoded by this ear and VOR eye movements related to the probe component are generated. However, if right-side horizontal canal function is absent, then neither ear is able to encode the probe component motion, and no VOR eye movements related to the probe component are generated. The absence of VOR eye movements related to the probe component is indicative of the absence of right-side vestibular function.

Figure 2:
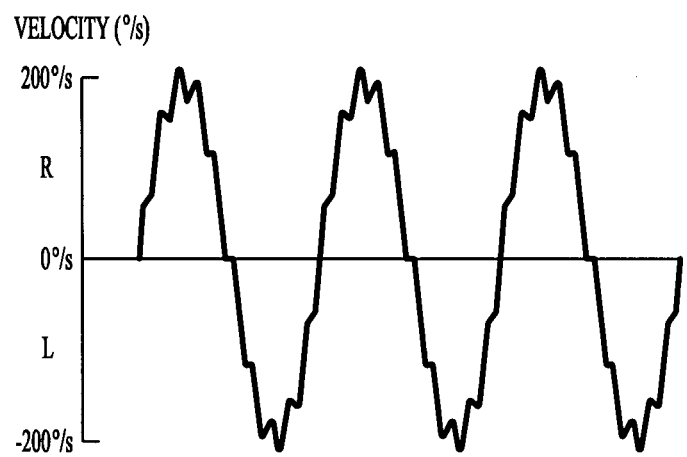
FIG. 2 illustrates an embodiment for a two-sine rotational stimulus, in accordance with the teachings of the present invention.

In an embodiment using the first type of rotational stimulus, the first rotational stimulus is designed to operate with lower torque motors commonly used in conventional clinical rotation test systems. In an embodiment, the first type of rotational stimulus is a two-sine stimulus. This first type of rotational stimulus includes two sinusoidal components, as shown in FIG. 2. In an embodiment of the two-sine, or 2-sine, stimulus, the bias component, or bias, is provided by a low frequency and high amplitude sinusoidal waveform relative to the probe component, or probe, which is added to the bias having a higher frequency and lower amplitude sinusoidal waveform than the bias. In an embodiment of the two-sine, or 2-sine, stimulus, the bias component, or bias, is provided by a low frequency (0.1 Hz or less) and high amplitude (150-250°/s peak velocity) sinusoidal waveform. The probe is added to the bias and includes a higher frequency (about 1 Hz) and lower amplitude (10-20°/s peak velocity) sinusoidal waveform.

Figure 3A:
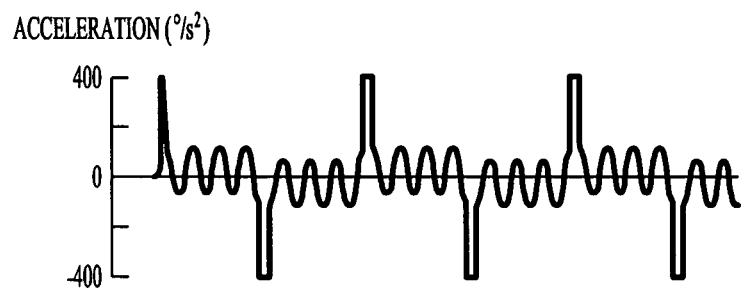
FIG. 3A illustrates an embodiment of an acceleration pulse, step, and sinusoidal for a pulse-step-sinusoidal (PSS) rotational stimulus, in accordance with the teachings of the present invention.
Figure 3B:
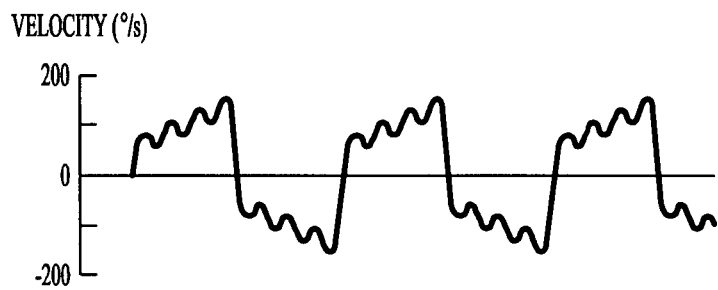
FIG. 3B illustrates an embodiment of a velocity waveform for a pulse-step-sinusoidal rotational stimulus, in accordance with the teachings of the present invention.

In an embodiment using the second type of rotational stimulus, the second rotational stimulus uses a higher torque motor and thus its use would currently be limited to facilities that have chairs with higher torque motors. However, the second rotational stimulus produces a longer period of inhibition, which allows for a longer evaluation period, and better opportunity to assess the function of each ear. Therefore, the second rotational stimulus may provide better indication of asymmetry. In an embodiment, the second type of rotational stimulus is a pulse-step-sine, or PSS stimulus which includes a pulse, step, and sinusoidal waveforms, as shown in FIG. 3A-3B. In an embodiment of the PSS stimulus, the bias component, or bias, includes 2 parts: a short-duration acceleration pulse waveform, followed by a lower amplitude, longer duration acceleration step waveform. The probe component, or probe, has a sinusoidal waveform. In an embodiment, the probe waveform is added to the acceleration step portion of the bias component. In an embodiment using the PSS stimulus, the bias component includes a short-duration, acceleration pulse (about $400°/s^2$ amplitude lasting about 1 s), followed by a lower amplitude, longer duration acceleration step (about $30°/s^2$ amplitude lasting about 4 s). The probe component has a sinusoidal waveform (about 1 Hz with 20°/s peak velocity), which is added to the acceleration step portion of the bias component.

In an embodiment, a set of computer algorithms that are used to analyze the eye movements evoked by embodiments of the rotational stimuli. The principle of the analysis algorithms is that responses to the bias and probe components of the stimulus are isolated from one another and separately analyzed. Both of these bias and probe component analyses provide quantitative measures relevant to the determination of vestibular function in each ear.

The limitations of the existing clinical tests discussed above motivated the development of a new test based on a novel rotational stimulus. The rotational stimuli are designed to take advantage of the 3D arrangement of the three pairs of semicircular canals in the two ears, and the physiological properties of the 8th nerve afferents innervating each semicircular canal. Each canal can be considered to be a fluid filled ring lying in a plane with a specific orientation in the head, and with respect to the other canals. Each canal plane can be defined by a vector perpendicular to that plane. For a given head rotational velocity characterized by a vector aligned with the axis of rotation, afferent nerves innervating a canal will generate a response that depends on both the magnitude of the rotation and the orientation of the head rotation vector relative to the canal vector. Specifically, each canal responds only to the component of the head rotation vector aligned with the canal vector (i.e. the projection of the head rotation vector onto the canal vector).

Semicircular canal orientation. The canals in opposite ears are pair-wise oriented and they operate in a push-pull manner. The horizontal canals in the two ears lie in approximately the same, roughly horizontal plane. A head rotation towards the left (herein, a positive rotation by convention) causes an increase in discharge rates of all left canal afferents, and a decrease in discharge rates of all right canal afferents. A head rotation to the right produces the opposite result. The remaining two pairs of vertical canals (left anterior—right posterior, and right anterior—left posterior) are oriented approximately perpendicular to the horizontal canal pair, perpendicular to one another, and about 45° with respect to the midline. A perfect mutually perpendicular organization of canal pairs would allow for stimulation of only one set of canals at a time if the head were positioned with the axis of rotation collinear with the orientation vector for that canal pair. However, in reality, both the perpendicular organization between canal pairs and the coplanar orientation within canal pairs is only approximate. The extent of this misalignment is of interest since it is likely to influence the sensitivity of the proposed new rotation test.

Semicircular canal afferent physiology. Head rotational motion is encoded by a change in the discharge rate of canal afferents from their resting rate. Primary afferents exhibit a variety of dynamics, but can be approximately represented by a first order high pass filter with a time constant of 4 to 7 s (considering the input to be rotational velocity). Typical canal afferents in the squirrel monkey have resting discharge rates of about 90 spikes/s. The discharge rate in humans is unknown, but presumably is similar to the monkey.

The existence of a high resting discharge rate means that each canal afferent can encode both positive and negative velocities. However, depending on the sensitivity of a given afferent, a large enough rotation in the inhibitory direction can silence neural activity in that afferent. Once silenced, that afferent is no longer proportionally encoding the rotational motion. In a subject with functional canals in both ears, rotational motion that inhibits neural activity in one canal's afferents excites activity in the opposite ear's paired canal. Since excitatory neural activity can achieve high rates (350-400 spikes/s) before saturating, the overall change in activity in paired canals (e.g. the difference between left and right side canal activity) monotonically encodes the amplitude of the rotational stimulus. However, the same is not true if vestibular function in one ear is absent. In this case, for horizontal plane rotations toward the bad ear, the neural activity in the horizontal canal of the good ear will decrease, silencing an increasing proportion of the afferents as the rotational velocity increases. In contrast, during rotations toward the good ear, the rotational motion is accurately encoded by the increasing discharge rate of the afferents in the only functional horizontal canal. The question is how to design a rotational stimulus that can demonstrate the expected asymmetry associated with unilateral vestibular dysfunction without requiring excessive acceleration or velocity.

In an embodiment, a stimulus is provided to take advantage of peripheral nonlinearities. Push-pull action of semicircular canal pairs results in maximal excitation of afferents in one canal and maximal inhibition of the canal afferents in the opposite ear. Canal afferents are more easily driven to cutoff (zero discharge rate) than to saturation (maximal discharge rate). Once afferents are driven to cutoff, they cannot encode a change in rotational motion.

Various embodiments are constructed using the hypothesis that unilateral vestibular dysfunction can be characterized using a clinically practical rotational stimulus that minimally includes two components. A 2-sine stimulus and collected data is described below to illustrate the principle of this new type of stimulus. It is anticipated that embodiments as described herein can be extended to other stimulus configurations, including a three-component stimulus. In an embodiment, a three-component stimulus includes a PSS stimulus.

In an embodiment, a two-sine stimulus includes two sinusoidal components. The first component is the low frequency bias component and the second component as the high frequency probe component. In an embodiment, the purpose of the bias component is to generate a large cyclic shift in the discharge rate of afferents innervating one canal pair using a low frequency (for example 0.1 Hz), higher amplitude rotation. A high amplitude, low frequency bias component is used to drive the activity in one canal to zero during a portion of each stimulus cycle. Based on animal studies, in an embodiment, a 0.1 Hz sinusoidal rotation with a 150-250°/s peak velocity is taken to be of sufficient magnitude to drive horizontal semicircular canal activity to zero.

The probe component is added to the bias component to provide the 2-sine stimulus. In an embodiment, the purpose of the probe component is to test the sensitivity of the system during different portions of the 10 s period of the bias component using a high frequency, low amplitude sinusoid (1 Hz, 20°/s in an embodiment). A low amplitude, high frequency probe component is used to test the ability of the vestibular system to encode this probe component throughout the entire stimulus cycle. If canal function is absent in one ear, and the bias component rotation drives the canal activity of the remaining good ear to zero, then motion due to probe component will not be encoded and VOR eye movements related to the probe component will be absent. For horizontal semicircular canals and VOR, the probe component response will be reduced or absent during the bias component rotation toward the dysfunctional ear. Use of a 1 Hz, 20°/s sinusoidal probe motion provides a good compromise between adequate signal-to-noise and motor torque requirements.

FIGS. 4A-C shows a schematic response to a 2-sine stimulus 400 (FIG. 4A) in a normal subject 410 (FIG. 4B) and in a right side unilateral loss subject 420 (FIG. 4C). VOR eye movements do not show modulation related to the high frequency probe component during rotations toward the dysfunctional ear in the unilateral loss subject. If the amplitude of the 0.1 Hz component is adequately large, some proportion of afferents in the right and left horizontal semicircular canals (RHC and LHC) will be silenced during a portion of the 10 second (10 s) cycle period. In a subject with normal canal function in both ears, it is expected that in this embodiment the VOR will be related to combined activity in both ears (the simplest possible model for combination is the difference between the two canal signals). Therefore, the 1 Hz modulatory influence of the probe component should be evident in the VOR eye movements recorded throughout the 10 s cycle. When a subject with no responsiveness in the right ear is tested using the same stimulus, some proportion of LHC afferents are unable to encode (due to silencing of their discharge) the rotational motion associated with the 1 Hz probe component during a portion of the 10 s cycle period when the subject is rotating toward the abnormal ear. Since the RHC encodes no motion at all, it is expected that in this embodiment the 1 Hz modulatory effects of the probe component will be reduced or absent in the VOR eye movements during rotations toward the defective ear. In contrast, during rotations toward the intact left ear, the LHC neural activity is able to encode both the bias and probe components, and the VOR eye movements will contain a 1 Hz component corresponding to the probe component of the stimulus.

In theory, the 1 Hz modulation would only be completely absent if activity in all LHC afferents contributing to the VOR were driven to silence. In practice, it may not be necessary or practical to silence all activity in order to develop a useful clinical test stimulus.

The magnitude of the rotational stimulus required to drive the discharge rate of afferents to zero depends upon both the resting discharge rate and sensitivity of the canal afferents. These values are unknown in humans, but are known in some animal models. In the squirrel monkey, for example, the mean resting discharge rate is about 90 spikes/s (s.d. 36) and the mean sensitivity to a rotational acceleration is 2.24 spikes·$s^{-1}$/deg·$s^{-2}$ (range 0.5-4). Taking into account the dynamic properties of the canals, one can predict that an average squirrel monkey horizontal canal afferent would be driven to silence during the peak inhibitory portion of a 0.1 Hz sinusoidal rotation with a peak velocity of 210°/s. Since there is little correlation between resting discharge rate and neural sensitivity, a 0.1 Hz rotation with a 210°/s peak velocity should silence about ½ of all horizontal canal neurons during a portion of the inhibitory half cycle of the stimulus. If human canal neurons have similar properties to squirrel monkey canal neurons, one would expect to see considerable VOR asymmetries in response to the two-component stimulus in patients with absent or reduced vestibular function in one ear.

The limitations of vestibular function tests discussed previously indicate that no single existing test adequately answers the important diagnostic questions: 1) Is vestibular function normal or abnormal? 2) If abnormal, which ear or ears are affected? 3) How severe is the abnormality? 4) Is the abnormality stable or fluctuating? The inadequacy of existing tests can be partially resolved by performing multiple tests using several different methods. But this increases the cost of obtaining a diagnosis, and increased cost is difficult to justify in the current health care environment. The reality is that physicians often settle for a single test (typically the caloric test as part of a standard test battery) with all of its attendant limitations. Some physicians may choose not to test at all since their experience indicates that the existing tests have a limited ability to facilitate their diagnostic assessment.

Embodiments for methods and apparatus include rotation test procedures that overcome poor performance of conventional rotation testing in identifying unilateral vestibular dysfunction, but maintains all of the advantages of conventional rotation testing (non-provocative/non-nauseogenic and good test-retest reliability), and therefore, can address the four diagnostic questions described in the previous paragraph. In addition, various embodiments take advantage of existing low torque rotation test devices already found in most major medical centers. This permits rapid adoption of embodiments of this new test into clinical practice. Such embodiments for a rotation test procedure would effectively eliminate the need for caloric testing, simplify the selection of appropriate diagnostic tests, and eliminate redundant testing. The routine application of various embodiments of this test would result in improved diagnosis of unilateral vestibular dysfunction, and therefore, would foster improved treatment of patients with chronic disabilities that are sometimes associated with unilateral vestibular dysfunction.

Studies

Discussion of results to studies consists of six parts. First is a computer simulation illustrating the expected VOR responses to the 2-sine rotational stimulus described in the previous section with respect to FIGS. 4A-4C. Second is a demonstration that experimental VOR responses recorded using a 2-sine rotational stimulus are similar to the predicted simulation results. Third is a description of an embodiment of a data analysis procedure for parameterizing responses to the probe component of the 2-sine stimulus. Fourth are results from the probe component parameterization procedure applied to experimental data from 3 normal and 4 unilateral loss subjects. Fifth is a description of an embodiment of a procedure for analyzing the bias component response and the results of applying this procedure to normal and unilateral loss subject data. Sixth is a discussion of the applicability of the proposed stimulus and analysis procedures to subjects with partial unilateral loss of vestibular function.

VOR Simulation.

Figure 5:
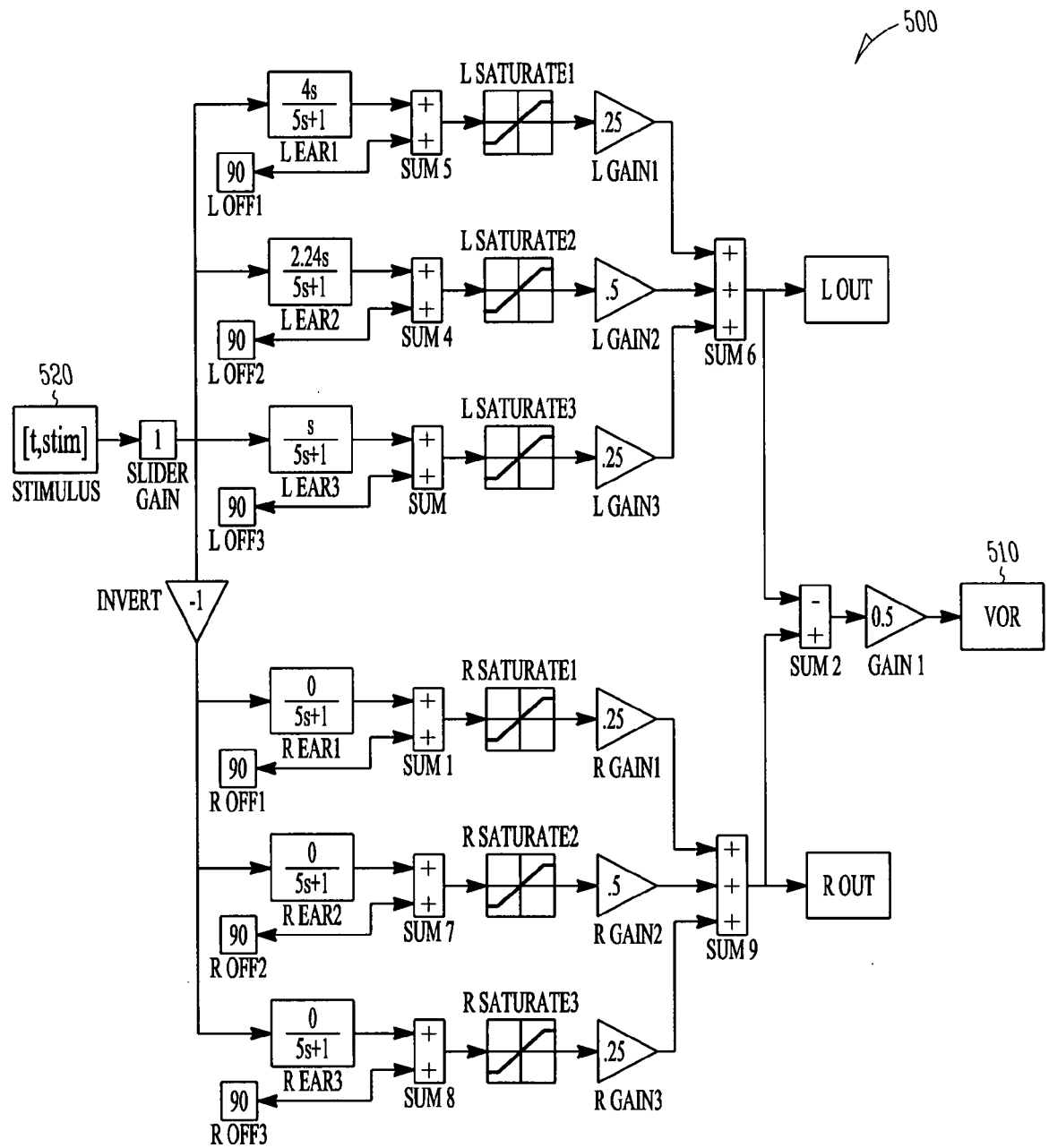
FIG. 5 shows a block diagram used to simulate VOR responses of an embodiment for testing, in accordance with the teachings of the present invention.

FIG. 5 shows a block diagram used to simulate VOR responses (implemented in Simulink, The MathWorks, Natick Mass.). Only the right and left horizontal canal pair is represented. The simulation 500 provides VOR response 510 to stimulus 520 and includes 3 weighted afferent channels in each ear. The weighting provides a rough approximation to a distribution of afferent properties. The input is considered to be head rotational velocity. In an embodiment, each channel includes a high pass filter with a 5 s time constant representing the dynamics properties of the canals. In this simulation, each afferent channel is assumed to have the same resting discharge rate of 90 spikes/s, but the sensitivity of each channel varies. The afferent channel with the largest weight of 0.5 is assigned an acceleration sensitivity of 2.24 spikes-$s^{-1}$/deg-$s^{-2}$. The other two channels, each with a weight of 0.25, are assigned sensitivities of 4 spikes-$s^{-1}$/deg-$s^{-2}$ and 1 spike-$s^{-1}$/deg-$s^{-2}$, respectively. The model parameters are based on physiological measures (for example afferent sensitivities and the mean discharge rate) in the squirrel monkey (See references 16 and 24 above). A saturation nonlinearity prevents afferent discharges from falling below zero spikes/s. The stimulus is assumed to be rotational velocity. All channels pass through a nonlinear element that clips the discharge rate at zero for rotational motions that inhibit the afferents, but permits unlimited positive discharge rates. Finally, the VOR eye velocity response output is assumed to be proportional to the discharge rate of all right side afferents minus all left side afferents. To simulate a complete unilateral absence of vestibular function, the sensitivities of all afferents in one ear are set to zero.

Various 2-sine rotational motions were used as inputs to this model. In an embodiment, the stimuli consisted of a 0.1 Hz low frequency bias component with amplitudes varying from 0°/s to 250°/s in 50°/s increments. In the embodiment, the high frequency probe component was always 1 Hz with a 20°/s amplitude. FIG. 6A-6F shows the simulated VOR output (simulated VOR slow phase eye velocity response to a 2-sine stimulus in normal and left unilateral loss subjects) for the embodiment of the simulation of FIG. 5. The bias component stimulus amplitude increased from 0 to 250°/s, but the probe stimulus amplitude remained constant. This simulated VOR output illustrates that no response asymmetry is grossly evident when the bias component amplitude was below about 100°/s. However, at higher bias component amplitudes, the response became increasingly asymmetric with reduced responses during rotations toward the absent ear.

FIGS. 7A-7E show the portion of the simulated VOR eye velocity related to the high frequency probe component for the embodiment of the simulation of FIG. 5. Simulated VOR probe responses to a 2-sine stimulus in normal and left unilateral loss subjects. The bias component amplitude increased from 0 to 250°/s. At higher bias component velocities, the response to the probe component decreased during rotations toward the dysfunctional left ear. The response to the probe component was separated from the bias component using a 0.5 to 5 Hz bandpass filter. For normal subjects, the probe component response was present throughout the 10 s period corresponding to one cycle of the 0.1 Hz bias component, although some "double modulation" distortion occurred at higher bias component amplitudes. This distortion consisted of a decrease in the probe component VOR during the two portions of the 10 s bias component cycle corresponding to the peak bias component velocity.

When the left ear sensitivity was set to zero to simulate a unilateral loss, the high frequency VOR component was present throughout the 10 s period only when the bias component amplitude was 100°/s and below. But when the bias component amplitude was increased (150 to 250°/s), the probe component VOR was reduced during the portion of the bias component cycle corresponding to rotation towards the dysfunctional ear.

Experimental Responses to 2-sine Stimulation.

Three normal and four unilateral loss subjects were tested using 2-sine stimuli identical to those used in the simulation study described above with respect to FIGS. 6A-6F and FIGS. 7A-7F. The unilateral loss subjects included subject UL1, a 66 year old female who had a left side acoustic neuroma removed by a trans-labyrinthine surgical approach 3 years prior to testing, subject UL2, a 46 year old male with a 3 cm left side acoustic neuroma treated with a "gamma knife" radiation procedure 3 ½ years prior to testing, subject UL3, a 27 year old male with right side absent vestibular function, as determined by caloric testing (Meningitis contracted during infancy is believed to be the cause of this right side loss), and subject UL4, a 47 year old female with a right labyrinthectomy performed 3 months prior to testing as treatment for Meniere's disease.

All 4 unilateral loss subjects were well compensated as judged by their responses to conventional rotation tests (0.05, 0.2, and 0.8 Hz sinusoidal rotations with 60°/s peak velocity). Three of the four unilateral loss subjects showed abnormally advanced VOR response phase at 0.05 Hz (>20° phase lead). The fourth subject's (UL1) phase was advanced relative to center normal, but was not outside of the established lab normal range. Phase advance is typically the only abnormal finding with conventional rotation testing in well compensated unilateral loss subjects. However, this abnormal finding does not provide any information regarding the side of the vestibular loss.

All of the test stimuli were well tolerated by the three normal and four unilateral loss subjects tested to date. No discomfort, disorientation, or motion sickness symptoms were reported throughout the test sessions which lasted about 2 hours. Following testing, there were no complaints of imbalance, and none of the subjects had difficulty walking or maintaining stance.

FIGS. 8A-8F show the VOR slow phase horizontal eye velocity data recorded from one representative normal subject and the four unilateral vestibular loss subjects in this embodiment to a 2-sine simulation. These experimental responses are qualitatively similar to the simulation results (FIGS. 6A-6F). The experimental VOR slow phase eye velocity responses to 2-sine stimuli with the bias component amplitude increasing from 0 to 250°/s. Results are shown for two subjects with a left unilateral loss (UL1 & UL2), two subjects with a right unilateral loss (UL3 & UL4) and one normal subject (N1). The normal subject showed symmetric VOR responses for rightward and leftward directed rotations that increased with increasing stimulus velocity. The response to the 1 Hz probe component for the normal subject was evident throughout the entire 10 s cycle of the bias component.

Three of the four unilateral loss subjects (UL1, UL2, UL4) showed reasonably symmetric responses when the bias component amplitude was 50°/s. Responses of the unilateral loss subjects resembled normal subject responses for bias component amplitudes of 0 and 50°/s. Subject UL3 began to show some asymmetry even at a 50°/s bias component amplitude. In contrast to the normal subject responses, the asymmetry increased for all UL subjects as the bias component amplitude increased. This asymmetry was always such that the VOR eye velocity was reduced during rotation toward the dysfunctional ear. At higher bias component amplitudes, the VOR response to the probe component was not uniform throughout the 10 s bias component cycle, but was reduced during the portion of the bias component cycle when the subject was rotating towards the dysfunctional ear. Responses of the unilateral loss subjects showed saturation during rotation toward the absent ear at higher bias component amplitudes.

FIGS. 9A-9F show the modulation of the VOR response to the probe component with the VOR slow phase velocity data filtered using a 0.5 to 5 Hz bandpass filter. Experimental VOR probe responses to 2-sine stimuli with the bias component amplitude increasing from 0 to 250°/s. Results are shown for the two subjects with a left unilateral loss (UL1 & UL2), the two with a right unilateral loss (UL3 & UL4), and the one normal subject (N1) of FIGS. 8A-8F. VOR modulation of the probe response is diminished during rotations towards the dysfunctional ear. The unilateral loss subjects showed a systematic modulation of the VOR probe component amplitude over the 10 s bias component cycle. This modulation increased with increasing bias component amplitude. In contrast, the normal subject did not show a systematic increase in probe component modulation with increasing bias component amplitude. Additionally, the normal subject did not show the "double modulation" evident in the simulated VOR responses at the 200 and 250°/s bias component velocities, indicating that the simple model in FIG. 5 does not fully capture actual VOR behavior. All 3 normal subjects tested had results similar to those shown in FIGS. 9A-9F.

Analysis

Figure 10A:
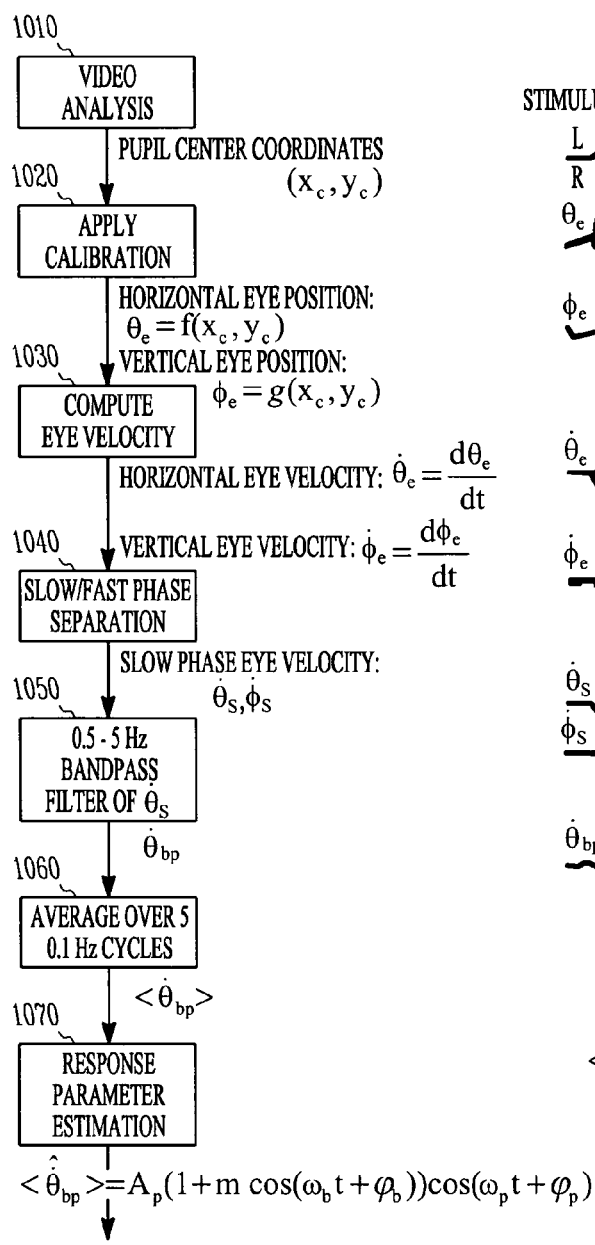
FIG. 10A depicts a block diagram of an embodiment for analysis of a probe component, in accordance with the teachings of the present invention.
Figure 10B:
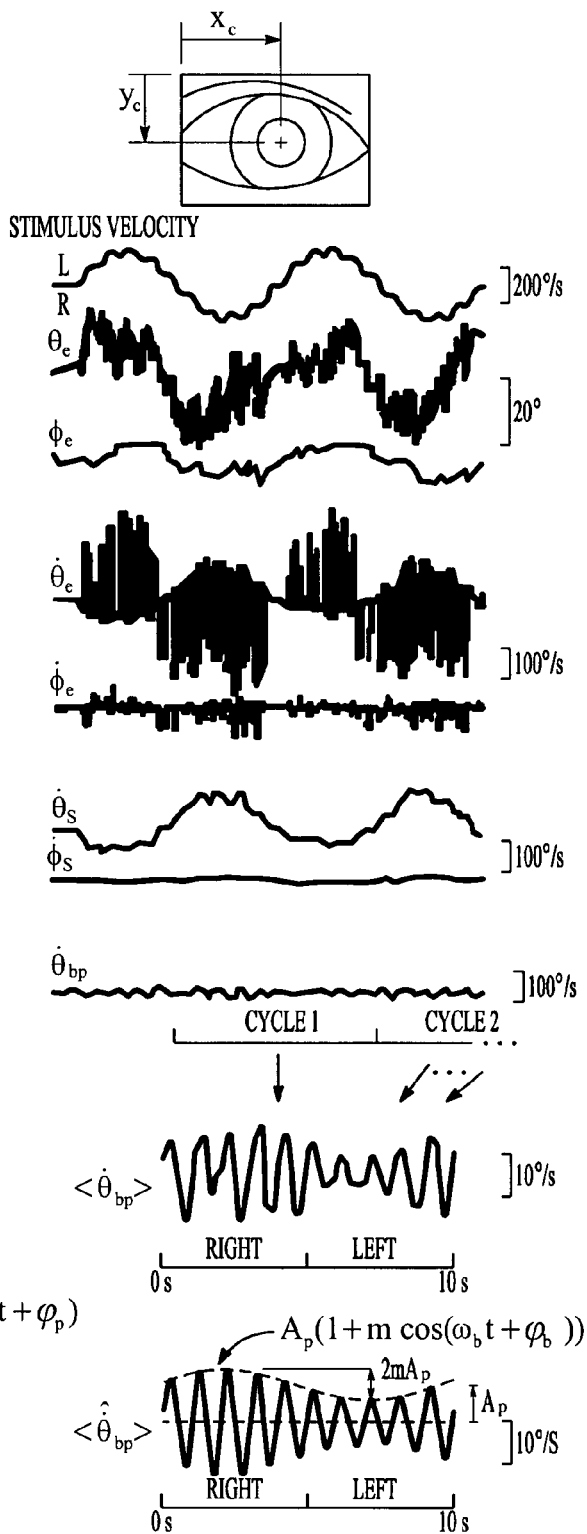
FIG. 10B illustrates data from a subject of FIGS. 9A-9F corresponding to the block diagram of FIG. 10A, in accordance with the teachings of the present invention.

FIG. 10A depicts a block diagram of an embodiment for analysis of a probe component. The flow diagram for the embodiment of the method shown in FIG. 10A is used to characterize the response to the probe component portion of the VOR. Example data in FIG. 10B are from subject UL1 of FIGS. 9A-9F, with a left side unilateral loss, tested with a 200°/s bias component amplitude. The analysis includes both standard methodology, typically applied to VOR analysis, and novel methodology used to separate and analyze the probe response. A video analysis is performed, at 1010, to acquire pupil center coordinates ($x_c$, $y_c$) and a calibration is applied, at 1020, to provide a horizontal eye position and a vertical eye position as a function of the pupil center coordinates ($x_c$, $y_c$) The standard portion of the analysis includes calculation of eye velocity from eye position data, at 1030, and separation of the slow and fast phases of nystagmus in order to obtain slow phase eye velocity, at 1040. The novel aspects of the analysis include bandpass filtering to isolate the response to the probe component of the stimulus, at 1050, and parameterization of the probe response, at 1070. As shown in FIG. 10A, after filtering, at 1050, the filtered signal may be averaged, at 1060, such as averaging over five 0.1 Hz cycles. In an embodiment, the parameterization of the probe response uses a curve fit. In an embodiment, the curve fit, the probe response fit, to the filtered and averaged VOR data uses the following equation:

$$\langle \hat{\theta}_{bp} \rangle = A_p(1+m\cos(\omega_b t+\phi_b))\cos(\omega_p t+\phi_p) \qquad \text{(eqn. 1a)}$$

$$\langle \hat{\theta}_{bp} \rangle = A_p(1+M(t))\cos(\omega_p t+\phi_p) \qquad \text{(eqn. 1b)}$$

In an embodiment, the bandpass response is filtered over a number of cycles of the bias component. In an embodiment, the bandpass response is filtered over five 0.1 Hz cycles.

In an embodiment, the curve fit is performed using a constrained nonlinear optimization procedure "const" available in the Matlab Optimization Toolbox (the curve fit actually includes sine and cosine components from which the phase of the response relative to a cosine reference is calculated). This equation represents an amplitude modulation (AM) operation used to describe communication systems where a "carrier" waveform, represented here by the probe frequency ($\omega_p$), is modulated by a lower frequency waveform using a multiplicative operation. In this case the lower frequency modulation occurs at the bias component frequency ($\omega_b$). The fit parameters include the probe component eye velocity amplitude ($A_p$), and the modulation function, M(t) where $$M(t)=m \cos(\omega_b t+\omega_b)$$

with m being a modulation factor, which can vary from 0 to 1, representing the depth of modulation of the probe frequency, the probe component phase, $\omega_p$, and the phase of the modulation waveform, $\omega_b$. Modulation factor, m, is related to the severity of the unilateral asymmetry. Modulation phase, $\omega_b$, indicates the side of unilateral loss. In an embodiment, $A_p$ equals the 1 Hz probe component eye velocity amplitude and m equals the modulation factor representing the depth of modulation of the probe component eye velocity.

Figure 11:
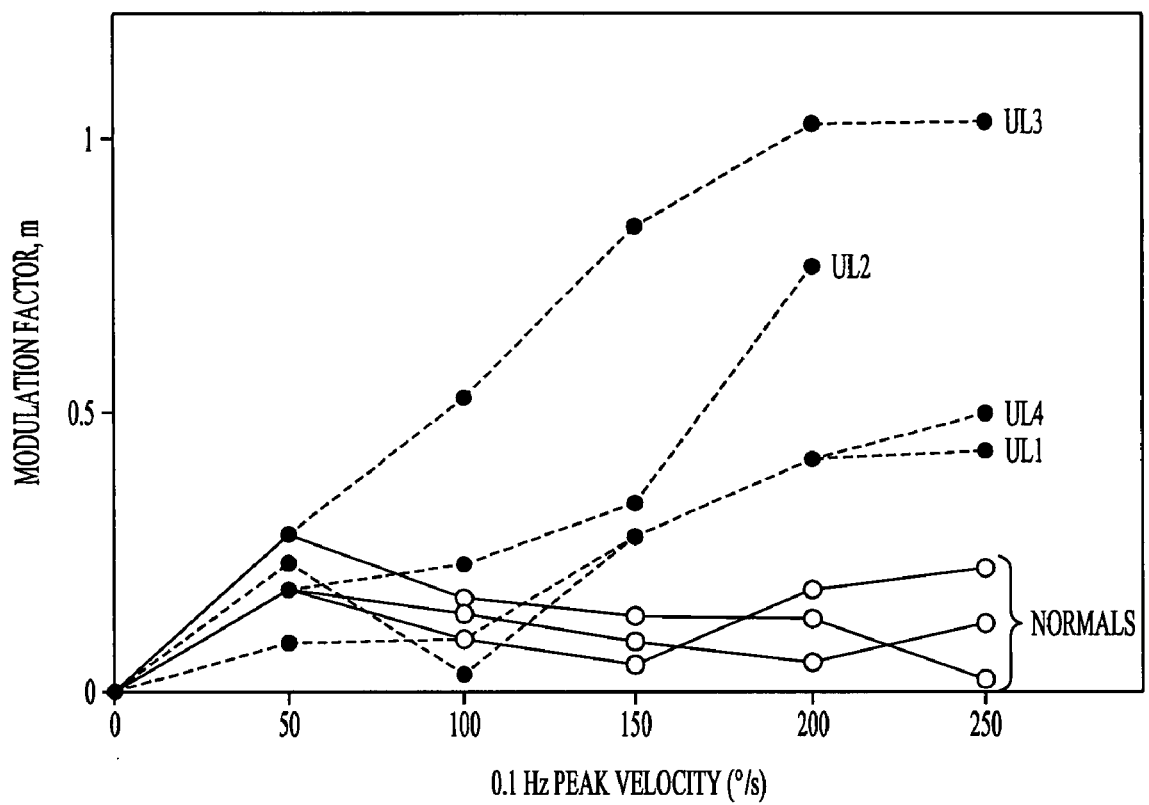
FIG. 11 shows a plot of the modulation factor, m, for the three normal and four unilateral loss subjects of the experiment related to FIGS. 8A-8F and FIGS. 9A-9F as a function of the bias component stimulus amplitude, in accordance with the teachings of the present invention.

FIG. 11 shows a plot of the modulation factor, m, for the three normal and four unilateral loss subjects of the experiment related to FIGS. 8A-8F and FIGS. 9A-9F as a function of the bias component stimulus amplitude. It can be seen that at lower bias component amplitudes, this parameter is unable to distinguish between normal and unilateral loss subjects. However, a clear separation is evident between subject UL3 and normals at a bias component amplitude of 100°/s, and at 150°/s all four unilateral loss subjects are distinguishable from normals. The modulation parameter increases with increasing bias component amplitude. For subject UL3, the modulation parameter saturated at 1 (full modulation) for the 200°/s and 250°/s bias component amplitude.

There are two important considerations regarding these preliminary results. First, the distortion of the probe component occurred at lower bias component amplitudes than indicated by the simple simulation model based on squirrel monkey afferent properties. This suggests that humans have either higher canal afferent sensitivity, or lower canal afferent resting discharge rates than the squirrel monkey. Whichever is the case, this apparent difference in physiology is advantageous in designing a new rotation test based on a 2-sine stimulus, since lower and presumably more tolerable bias component amplitudes should be adequate for the this new test. In addition, a lower peak stimulus amplitude evokes lower velocity eye movements, and this improves the likelihood that slow and fast phase components of nystagmus can be successfully separated from one another.

Second, two of the unilateral loss subjects shown in FIG. 11 (UL1 and UL4) had modulation factors that reached values of only 0.4 to 0.5 at the highest bias component amplitudes. Subject UL1's head was in a comfortable upright position during testing, and was not oriented in the approximately 20° nose down position that is expected to align the horizontal canals perpendicular to the axis of rotation. Therefore, the failure to obtain a large modulation factor for this subject at high bias component amplitudes may be due to the contribution of partially stimulated vertical canals contributing to the generation of horizontal eye movements. An attempt was made to align subject UL4's head for maximal horizontal canal stimulation; however, this alignment was not fully accomplish this due to limitations in procedures. Subsequent design of a head restraint system enables the systematic control of the head alignment.

Additional preliminary data indicates that head orientation does affect the modulation factor in unilateral loss subjects. For example, for subject UL4 tested with a bias component amplitude of 200°/s, m increased from 0.42 to 0.58 with a head tilt of 5° in a direction expected to bring the horizontal canals into better alignment. For subject UL3, also tested with a 200°/s bias component amplitude, m decreased from 1.0 to 0.81 when the head was reoriented by 5°. Therefore, head orientation appears to be an important factor influencing the sensitivity for various embodiments of the rotation test. The influence of head orientation can be systematically investigated using both modeling and experimental methods.

With respect to the probe component responses of FIGS. 9A-9F, for the normal subjects, there was little or no modulation over the course of the bias component cycle. The modulation factor, m, increased only slightly with increasing bias component amplitude. Further, for the normal subjects, estimates of the probe-related slow phase eye velocity were noisiest during the high velocity portions of the bias component cycle. Increased noise was due to increased high frequency nystagmus.

With respect to the probe component responses of FIGS. 9A-9F, for the unilateral loss subjects, modulation factor, m, increased with increasing bias component velocity. Probe response amplitude was smallest for these subjects during bias component rotation toward the absent ear. For the unilateral loss subjects, estimates of the probe-related slow phase eye velocity were noisiest during the high velocity portion of the bias component cycle when the subject was rotating toward the good ear. This noise likely caused increased variability in the estimation of m, and this variability increased with increasing bias component amplitude.

The VOR responses to the 2-sine stimuli in FIGS. 8A-8F show that the overall response was quite asymmetric and distorted for the unilateral loss subjects compared to the example normal subject at higher bias component amplitudes. For this preliminary data from subjects with complete unilateral loss, it appears that a larger amplitude sinusoidal stimulus alone (i.e. without the probe component) would adequately identify the side of the vestibular asymmetry. In the next section, simulation results are used to argue that this may not be the case in subjects with a partial unilateral loss. Nevertheless, at this point, it is reasonable to analyze data in all ways that seem likely to contribute to the identification of asymmetric function.

Figure 12:
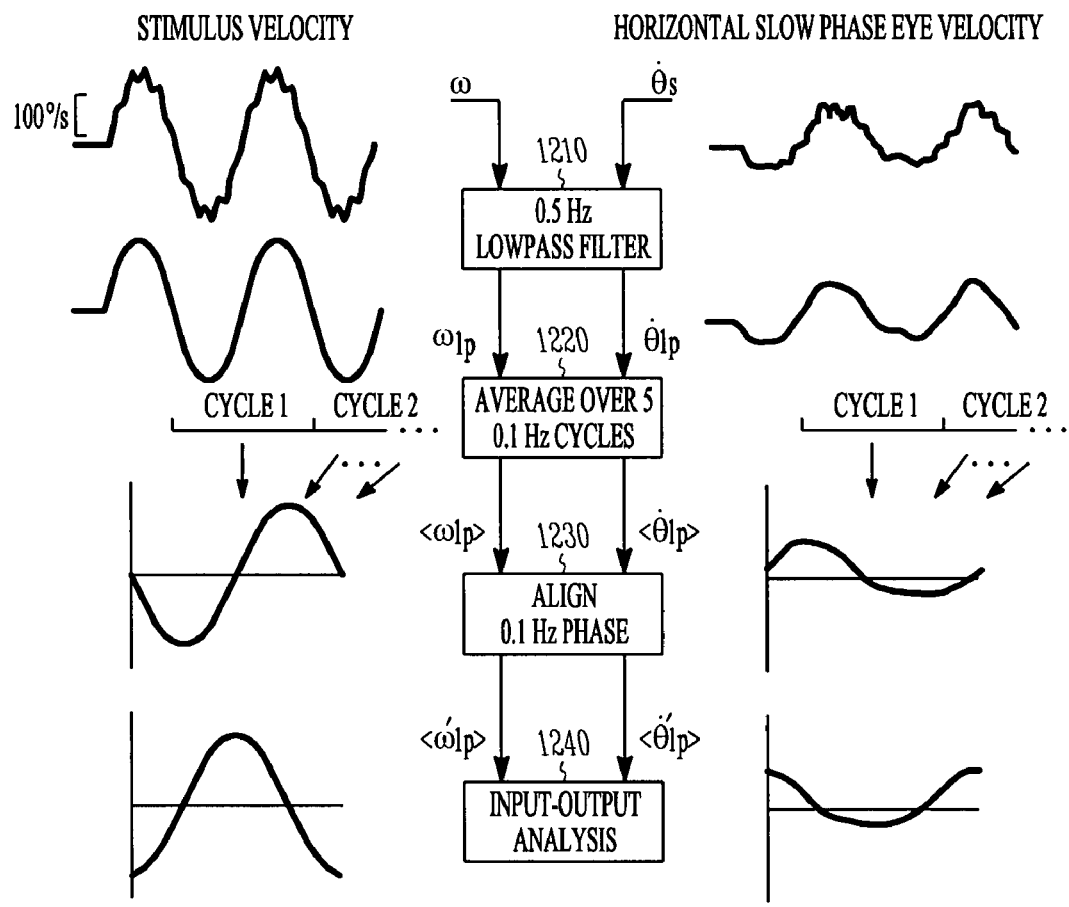
FIG. 12 depicts a block diagram of an embodiment of a method to analyze the bias components of the 2-sine stimulus, in accordance with the teachings of the present invention.
Figure 13:
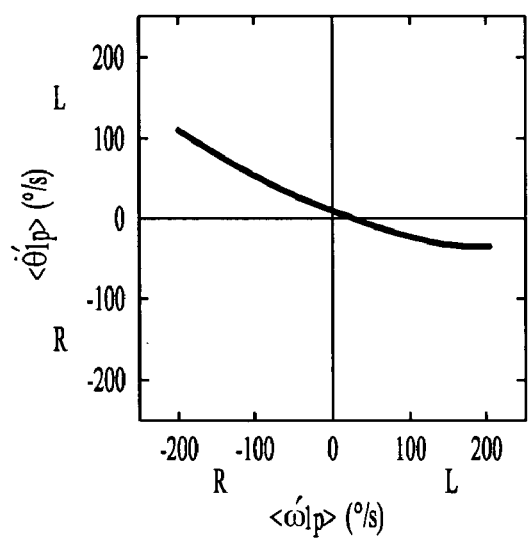
FIG. 13 shows an embodiment for a input-output relationship generated according to the embodiment in FIG. 12, in accordance with the teachings of the present invention.

FIG. 12 depicts a block diagram of an embodiment of a method to analyze the bias components of the 2-sine stimulus. The flow diagram for the embodiment of the method shown in FIG. 12 shows a procedure to analyze distortion in the bias component of the 2-sine stimulus. This method may be related to methods previously used to analyze VOR gain asymmetries. Example data in this figure are from subject UL1 in FIGS. 8A-8F tested with a 200°/s bias component amplitude. At 1210, slow phase eye velocity and stimulus velocity data are low pass filtered (in an embodiment, a low pass filter having a 0.5 Hz cutoff is used) to remove the probe component from both the stimulus and VOR response waveforms. At 1220, the data is averaged over a number of cycles of the bias component. In an embodiment, the data are then averaged over five 0.1 Hz cycles. In an embodiment, the data are then averaged over consecutive 10 s periods corresponding to the bias component cycle period. A discrete Fourier transform is used to estimate the phase of the stimulus and response waveforms at the bias component frequency. At 1230, these waveforms are then time shifted so that they are aligned with a 180° phase shift between them (reflecting the compensatory nature of the VOR). Finally, at 1240, a negatively sloped input-output function is obtained by plotting the eye velocity versus the stimulus velocity. FIG. 13 shows an embodiment for a input-output relationship generated according to the embodiment in FIG. 12. In an embodiment, deviations of this input-output function from a straight line indicate the presence of nonlinear system effects, in this case a saturation-type nonlinearity where the eye velocity is attenuated at higher velocities of rotations toward the ear with absent vestibular function.

Figure 14:
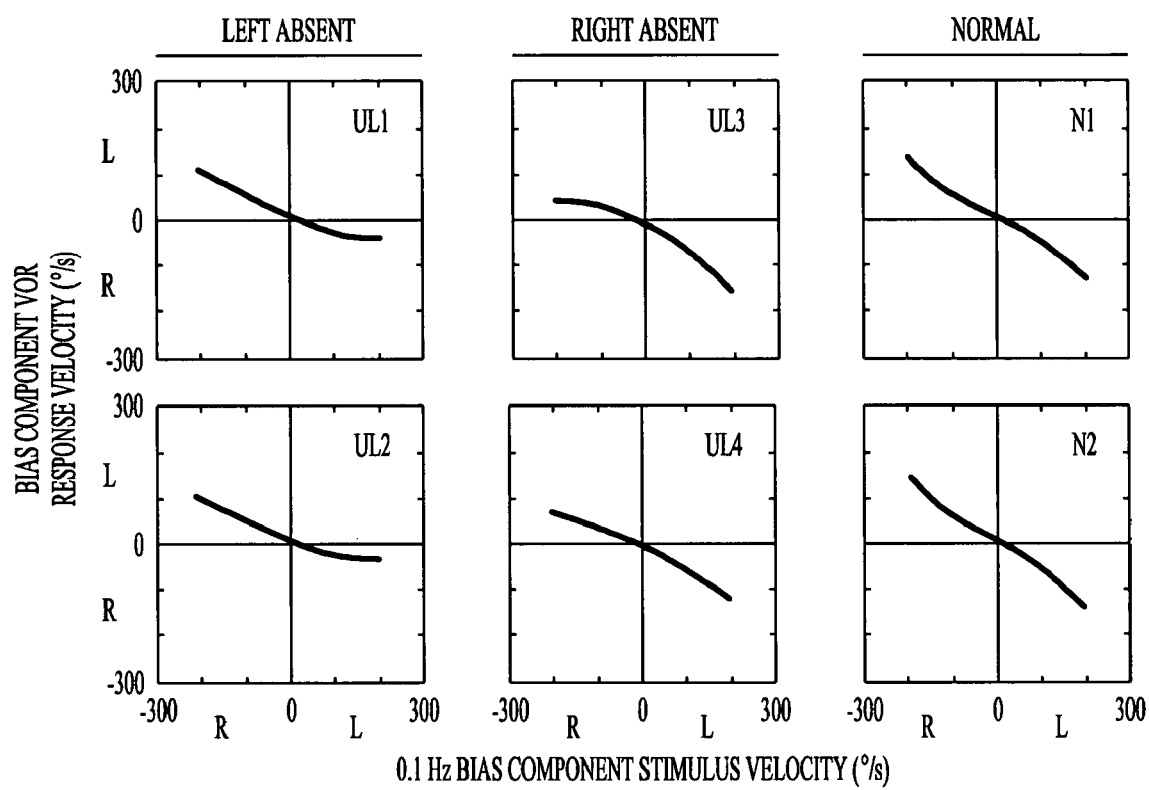
FIG. 14 shows the results of an embodiment of the input-output analysis of FIG. 12 for the four unilateral loss subjects and two normal subjects of FIGS. 8A-8F, in accordance with the teachings of the present invention.

FIG. 14 shows the results of an embodiment of the input-output analysis of FIG. 12 for the four unilateral loss subjects and two normal subjects of FIGS. 8A-8F. All data in FIG. 14 are from a 2-sine stimulus with a 200°/s bias component amplitudes. In all unilateral loss subjects, rotations toward the dysfunctional ear produced a clear saturation-type nonlinearity compared to rotations toward the good ear. Consistent estimates of saturation amplitudes were obtained using 200 and 250°/s bias component stimuli, and often with 150°/s stimuli. The normal subjects had symmetric, although not entirely linear, input-output functions with no saturation.

Previous investigators have quantified similarly determined input-output functions by fitting two line segments to the input-output function with one line segment corresponding to positive stimulus velocities and the other to negative stimulus velocities. The slope of these line segments provide measures of VOR gain for rotations to the right and left. A VOR gain asymmetry measure can be obtained from these two gains using the formula 100*(GainR−GainL)/(GainR+GainL). The preliminary results show a clear saturation-type nonlinearity suggest that a two-part linear fit would not be a good choice. In an embodiment, a better candidate for fitting the input-output data would appear to be some type of saturating function such as:

$$\langle \hat{\theta}'_{lp} \rangle = \frac{K\left(1 - e^{-\beta \langle \omega'_{lp} \rangle}\right)}{1 + e^{-\beta \langle \omega'_{lp} \rangle}} \quad \text{(eqn. 2)}$$

where $\langle \hat{\theta}'_{lp} \rangle$ is a fit to the low pass filtered bias component eye velocity, $\langle \omega'_{lp} \rangle$ is the low pass filtered bias component stimulus velocity, and K and β are fit parameters related to the gain and saturation behavior of the input-output function. Parameter K is the saturation amplitude (°/s), β is the saturation rate, and $\langle \omega'_{lp} \rangle$ is the phase aligned bias component of the stimulus velocity. Since the saturation function given by eqn. 2 is symmetric about the origin, separate fits of this functional form would be required for rotations toward the right and left.

An important question is whether or not a 2-sine stimulus can be used to identify and localize a partial unilateral vestibular lesion. Simulation results based on FIG. 5 simulation model suggest that it can. Partial lesions were simulated by setting the gains of all afferent fibers in the left ear to some fraction of their normal value (afferent gains of 0.75, 0.5, 0.25, and 0 times normal values to simulate 25%, 50%, 75%, and 100% canal paresis, respectively). The simulation was run using a 2-sine stimulus with a 250°/s bias component amplitude and 20°/s probe component amplitude. The simulated eye velocity responses were analyzed using embodiments for the probe analysis and input-output analysis procedures of FIGS. 10A and 12.

The results of these analyses are shown in FIGS. 15A-15D. These simulation results show effects of increasing levels of unilateral vestibular dysfunction. The center column shows VOR probe component analysis of simulated data and the right column shows input-output bias component analysis. The probe response shows a clear relationship between the depth of modulation and the magnitude of the vestibular asymmetry. The input-output analysis also shows that the asymmetry of the bias component response increases with increasing vestibular asymmetry. However, it is easy to imagine that it would be difficult to detect a 25% or 50% canal paresis from the bias component input-output analysis in the presence of relatively small amounts of physiological variability in the eye velocity data. In contrast, the probe component response appears to be more robust. This result is consistent with the fact that the probe component analysis essentially provides an independent comparison of VOR gain at the peak positive and negative excursions of the bias component stimulus. These two peak points in the bias component stimulus cycle are most likely to be influenced by the existence of asymmetric vestibular function. In contrast, the input-output analysis of the bias component response is dominated by large portions of the input-output function which are likely to be symmetric even though a partial vestibular asymmetry exists.

Based on the preliminary results in subjects with a verified complete unilateral loss of vestibular function, an embodiment using rotational stimulus appears to be effective in unambiguously identifying the side of lesion. As can be appreciated by those skilled in the art, additional work can be performed to determine optimal stimulus design, investigate factors that influence test sensitivity and reliability, and apply the various embodiments for the rotational test to a larger group of subjects with varying levels of vestibular dysfunction.

In an embodiment for testing with a 2-sine stimuli, the frequency components are shown in Table 1. For each of the four frequency combinations, the amplitude of the bias component is be varied from 50°/s to 250°/s in increments of 50°/s while the probe component remains fixed in frequency and amplitude.

TABLE 1

2-sine stimulus frequency combinations

| | | Probe Component | |
|---|---|---|---|
| Stimulus # | Bias Component Frequency (Hz) | Freq (Hz) | Amp (°/s) |
| 1 | 0.025 | 1 | 20 |
| 2 | 0.05 | 1 | 20 |
| 3 | 0.1 | 1 | 20 |
| 4 | 0.1 | 2 | 10 |

A pulse-step-sine (PSS) stimulus, representing a form of 3-component rotational stimulus, can be applied to produce a large shift in the discharge rate of the primary afferents, followed by testing at the extremes of the discharge rate shift. The PSS stimulus provides a potentially optimal stimulus for rapidly displacing the afferent discharge rate, maintaining that discharge rate displacement at a constant level, and then testing the system. The PSS stimulus includes a short duration acceleration pulse followed by a lower amplitude, longer duration acceleration step. A sinusoidal probe component is added to the acceleration step. With proper selection of the acceleration pulse and step components, the afferent discharge rate will theoretically remain at a constant shifted level throughout the duration of the step phase of the stimulus. Therefore, the sinusoidal probe component can test the system while the afferent discharge rate is at a fixed displacement from the resting rate. This is in contrast to a 2-sine stimulus where the afferent discharge rate is continuously changing throughout the bias component cycle.

Figure 16A:
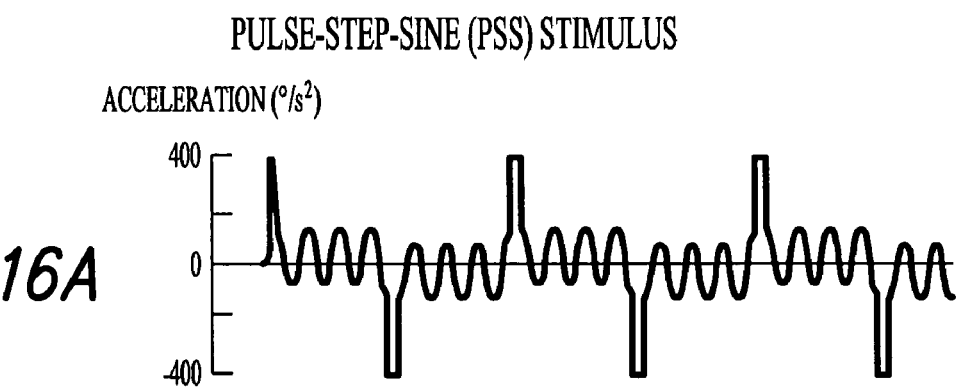
FIGS. 16A-16C show embodiments of the stimulus acceleration, velocity, and simulated semicircular canal afferent discharge rate profiles for a PSS stimulus, in accordance with the teachings of the present invention.
Figure 16B:
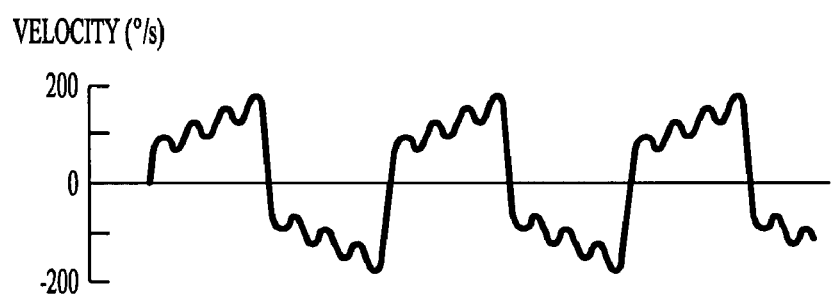
Figure 16C:
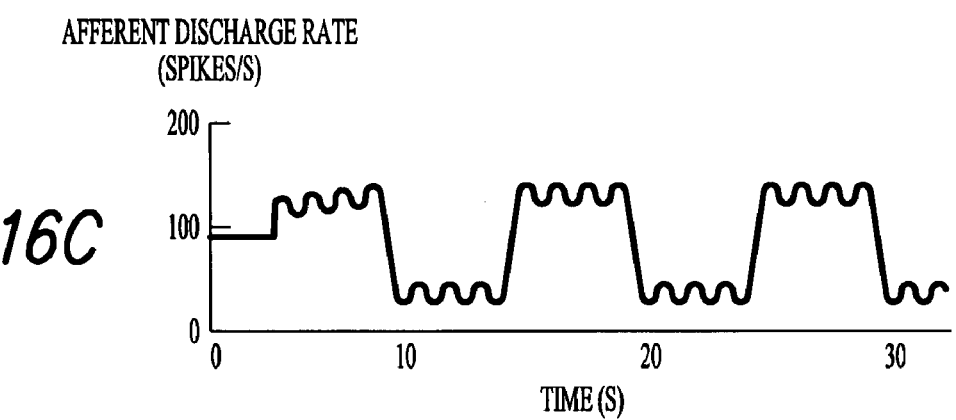

The stimulus acceleration, velocity, and simulated afferent discharge rate profiles for an example PSS stimulus are shown in FIGS. 16A-16C. The trace of FIG. 16A shows the rotational acceleration profile for the example PSS stimulus. The trace of FIG. 16B shows the velocity profile for the example PSS stimulus. The trace of FIG. 16C shows a simulated response to the PSS stimulus of an average squirrel monkey canal afferent. Variations in the pulse duration and amplitude determine the displacement of afferent discharge rates from resting levels. The acceleration step amplitude needed to maintain that displaced discharge rate is a function of the preceding pulse parameters and the time constant of the afferent nerve fibers. In an embodiment, a 5 s time constant is assumed in the stimulus design. The displacement of afferent discharge from the resting rate, ΔR, is given by:

$$\Delta R = S_{off} A_{pulse} \left(1 - e^{\frac{-t_p}{2\tau}}\right) \quad \text{eqn. 3}$$

where $S_{aff}$ is the acceleration sensitivity of the afferent, $A_{pulse}$ is the acceleration pulse amplitude of the PSS stimulus, $t_p$ is acceleration pulse duration, and τ is the afferent time constant.

As the amplitude of the preceding pulse increases, a larger step acceleration is needed to maintain a fixed discharge rate. Several cycles of a sinusoidal motion are added to the step component to provide a probe stimulus to test the VOR system while the afferents remain at a displaced discharge rate. Table 2 shows a series of PSS stimuli with each subsequent stimulus in the series producing a larger afferent discharge displacement. In an embodiment, the cycle length for each of these 4 stimuli is 10 s. The predicted displacement of afferent discharge is matched to the peak displacement predicted for the 0.1-1.0 Hz 2-sine stimuli with the 0.1 Hz bias component amplitude varying from 50°/s to 200°/s.

TABLE 2

PSS stimuli

| PSS Stimulus | Pulse Component | | Step Component | | Sine Component | | |
|---|---|---|---|---|---|---|---|
| | Amp (°/s²) | Duration (s) | Amp (°/s²) | Duration (s) | Freq (Hz) | Amp (°/s) | Cycles |
| 1 | 400 | 0.25 | 9.9 | 4.75 | 0.95 | 20 | 4.5 |
| 2 | 400 | 0.51 | 19.9 | 4.49 | 1.0 | 20 | 4.5 |
| 3 | 400 | 0.78 | 30.0 | 4.22 | 0.83 | 20 | 3.5 |
| 4 | 400 | 1.05 | 39.9 | 3.95 | 0.89 | 20 | 3.5 |

In an embodiment, PSS analysis involves measurement of the amplitude of the sine component for rotations to the right and left. An asymmetry measure (similar to the VOR gain asymmetry measure used to characterize conventional rotation test responses) calculated from these amplitude measurements would correspond approximately to the modulation factor, m, calculated from the probe analysis for the 2-sine stimuli. If the response to the sine component of the PSS stimulus is ignored (by low pass filtering), the remainder of the PSS slow phase velocity response should approximate a square wave (with rounded corners). A displacement of the mean value of this slow phase velocity waveform (mean calculated over an integer number of cycles) away from zero would be indicative of an asymmetry of this response, and would correspond approximately to the input-output analysis of the bias component of the 2-sine stimulus.

For the 2-sine test series, response parameters (e.g. m and parameters summarizing the asymmetry of input-output functions) may be plotted as a function of the bias component amplitude, as in FIG. 11. Similar plots may be made for measures derived from the PSS stimuli, with PSS response asymmetry measures plotted versus an equivalent to the bias component amplitude (specifically, the peak velocity amplitude of the fundamental frequency component of the PSS stimulus).

From the results in FIG. 11, it is anticipated that as the bias amplitude increases, there will be an increasing separation between asymmetry measures from normal subjects versus unilateral loss subjects. At each bias component amplitude, the mean, standard deviation, and range of response parameters for the normal and unilateral loss groups may be computed for each of the four different test series given in Table 1 and the PSS series in Table 2. Assuming approximately normal distributions, but not necessarily equal variances between the groups, a "threshold bias amplitude," defined as the point where the separation between results from the normal and unilateral loss group have a maximum 5% misclassification of normal subjects as abnormal and abnormal subjects as normal (95% specificity and 95% sensitivity), can be estimated. Test series may be compared by their threshold bias amplitudes. The series with the lowest threshold bias amplitude will be presumed to be the most sensitive test for detecting a unilateral vestibular asymmetry.

Other features of response parameter variation may also be considered. For example, saturation effects can be considered, as shown in the modulation factor data from subject UL3 in FIG. 11. It would be detrimental to choose a stimulus for clinical use that showed saturation effects in complete unilateral loss subjects since abnormal subjects with less than a complete unilateral loss might be indistinguishable from complete loss subjects.

Experimental Responses to a Pulse-Step-Sine Rotational Stimulus

In applying the PSS rotational stimulus, the application of this stimulus takes advantage of peripheral nonlinearities. The push-pull action of semicircular canal pairs results in maximal excitation of afferents in one canal and maximal inhibition of the canal afferents in the opposite ear. Canal afferents are more easily driven to cutoff (zero discharge rate) than to saturation (maximum discharge rate), and once afferents are driven to cutoff, they cannot encode a change in rotational motion.

In the PSS stimuli applied, the pulse component provides a rotational acceleration pulse that drives the activity in one canal toward zero during a portion of each stimulus cycle. An acceleration step maintains the canal nerve activity at a zero discharge rate throughout the duration of the step component. The sine component is a low amplitude, high frequency sine waveform that is added to the step portion of the stimulus. The sine component tests the ability of the vestibular system to encode this component throughout the step portion of the stimulus. If canal function is absent in one ear, and the pulse-step components drive the canal activity of the remaining good ear to zero, then motion due to the sine component will not be encoded and VOR eye movements related to the sine component will be absent. For horizontal semicircular canals and VOR, the sine component response will be reduced or absent during pulse-step component rotation toward the dysfunctional ear. Use of a 1 Hz, 20°/s sinusoidal component motion provides a good compromise between adequate signal-to-noise and motor torque requirements.

An experimental application using four different PSS stimuli (Table 2) included ten subjects with normal vestibular function, five subjects with complete unilateral vestibular loss (three left and two right), and one subject with asymmetric bilateral vestibular loss with the right side less than the left side. The testing of the subjects included rotation about earth-vertical axis in the dark and the head orientated 20° nose down from Reid's plane to place horizontal canal plane perpendicular to rotation axis. The parameters for the four PSS rotational stimuli were a pulse component having a 400°/s² amplitude with durations ranging from 0.25 to 1s, a step component having amplitudes ranging from 10 to 38°/s² with durations ranging from 4 to 4.8 s, and a sine component with either 3.5 or 4.5 cycles of approximately 1 Hz sinusoid with 20°/s amplitude (Table 2).

In normal subjects, the responses were symmetric for leftward and rightward directed rotations. Response to the sine component was evident throughout both rightward and leftward step components. In unilateral loss subjects, the responses resembled normal subject response for lowest amplitude PSS stimulus. The responses became increasingly asymmetric with increasing PSS amplitude with loss of the sine response during rotation toward the absent ear. In the asymmetric bilateral loss subject, the responses became increasingly asymmetric with increasing PSS amplitude with step component response showing the primary asymmetry.

Measures for PSS rotational stimulus are generated from slow/fast phase separation of eye velocity data and averaging over a number of cycles of the bias component of the stimulus, in which the response to the sinusoidal stimulus is isolated from the response to the pulse-step component.

PSS Bias (or Step) Component Measures.

Figure 17A:
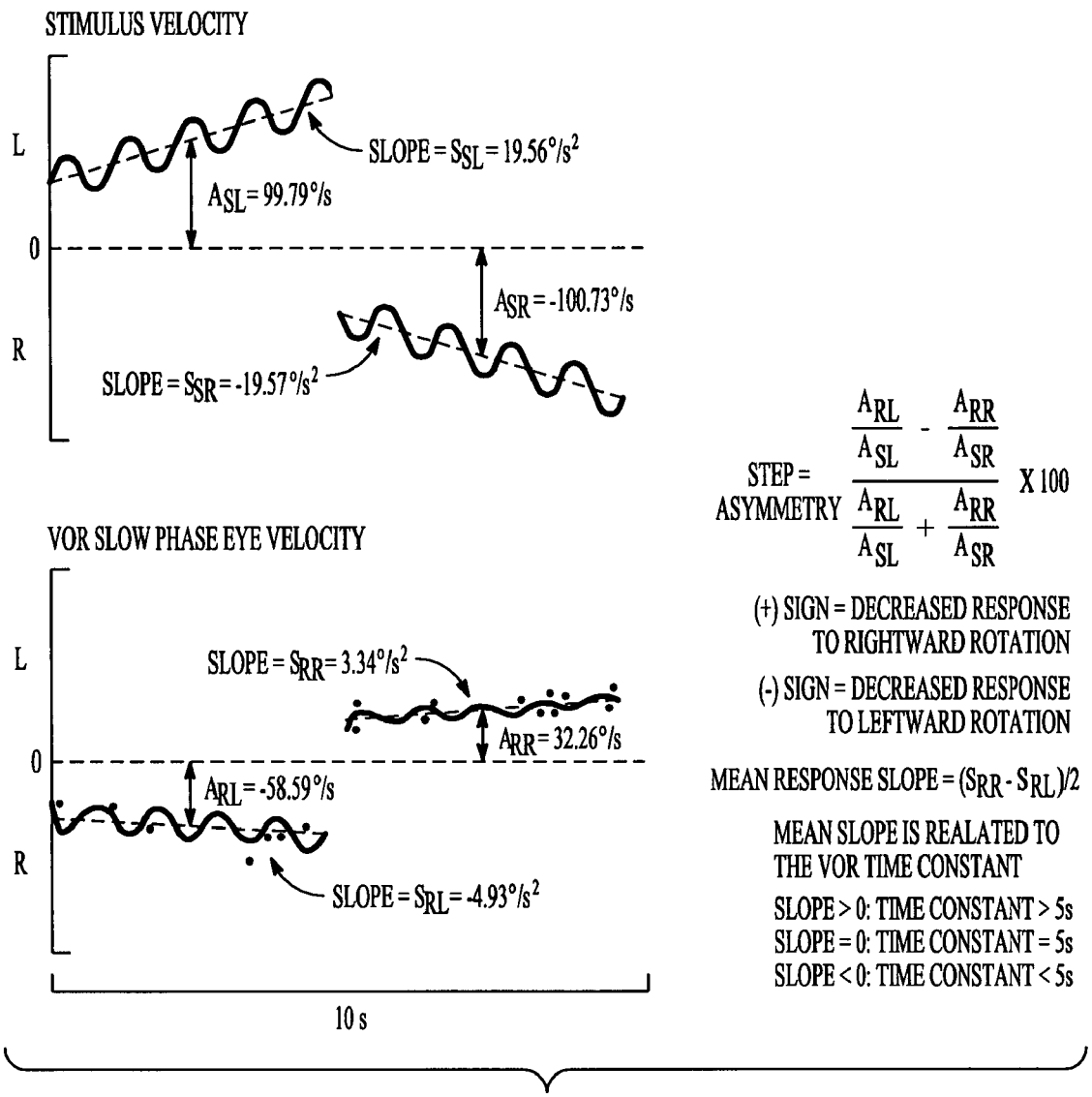
FIG. 17A shows an embodiment for step component measures for a test using PSS rotational stimulus, in accordance with the teachings of the present invention.

PSS step component measures are made from average slow phase eye velocity data obtained from the step portion of the pulse-step-sine stimulus. There are two measures. One is the "step asymmetry" and the other is the "mean response slope." The step asymmetry parameter gives a comparison of the difference in response gains for rotations that evoke leftward eye movements versus rotations that evoke rightward eye movements. A "gain" is defined as the ratio of the response velocity to the stimulus velocity. The equation is shown in FIG. 17A relative to the graphs for stimulus velocity and VOR slow phase eye velocity, where the parameters in this equation are:

- $A_{SL}$=average stimulus velocity (units °/s) during the leftward-moving step portion of the PSS stimulus. The subscript "S" stands for stimulus and the subscript "L" stands for leftward.
- $A_{SR}$=average stimulus velocity (units °/s) during the rightward-moving step portion of the PSS stimulus.
- $A_{RL}$=average VOR slow phase eye velocity (units °/s) during the leftward-moving step portion of the PSS stimulus. The subscript "R" stands for response and the subscript "L" stands for leftward and refers to the fact that this eye velocity is the average value measured during the leftward stimulus motion. The eye velocity is typically directed toward the right during a leftward stimulus motion.
- $A_{RR}$=average VOR slow phase eye velocity (units °/s) during the rightward-moving step portion of the PSS stimulus. The first subscript "R" stands for response and the second subscript "R" stands for rightward and refers to the fact that this eye velocity is the average value measured during the rightward stimulus motion. The eye velocity is typically directed toward the left during a rightward stimulus motion.

The mean response slope parameter is given by the equation:

$$\text{Mean Response Slope} = (S_{RR} - S_{RL})/2,$$

where $S_{RR}$ is the rate-of-change (i.e. a slope) of slow phase eye velocity (units °/s²) measured during the rightward-moving step portion of the PSS stimulus. The first subscript "R" stands for response and the second subscript "R" stands for rightward and refers to the fact that this eye velocity is the average value measured during the rightward stimulus motion. $S_{RL}$ is the rate-of-change (i.e. a slope) of slow phase eye velocity (units °/s²) measured during the leftward-moving step portion of the PSS stimulus. The subscript "R" stands for response and the subscript "L" stands for leftward and refers to the fact that this eye velocity is the average value measured during the leftward stimulus motion.

The mean response slope parameter is a measure that is related to a measure called the "VOR time constant" that is often obtained from responses to a conventional clinical rotation test. The value of a patient's VOR time constant can provide information about vestibular dysfunction. Specifically, a VOR time constant that is less than 5 seconds is typically associated with a bilateral loss of vestibular function. A time constant of 5 to 6 seconds is often associated with a unilateral vestibular loss. Finally, a time constant greater that about 8 seconds suggests normal vestibular function. The relation between the VOR time constant and the mean response slope is that subjects with a VOR time constant less than 5 seconds will have a slope with value less than zero. The mean response slope will be equal to zero if the VOR time constant is 5 seconds, and the mean response slope will be greater than zero if the VOR time constant is greater than 5 seconds. Therefore, this slope parameter provides equivalent information to that provided by an important parameter measured using conventional rotational stimuli. Other parameters, such as the step asymmetry and measures related to the probe component, go beyond what is available from conventional rotation tests and facilitate the identification of the side of the vestibular loss.

PSS Probe (or Sine) Component Measures:

The parameter called "sine component asymmetry" gives a comparison of the difference in VOR probe-component gains for rotations that evoke leftward eye movements versus rotations that evoke rightward eye movements. The equation for the sine component asymmetry is shown in FIG. 17B relative to the graphs for the sine response during leftward and rightward steps. This equation makes use of two VOR gain measures defined as:

$$VOR_L = R_L/S_L$$

$$VOR_R = R_R/S_R,$$

where:
- $R_L$=peak slow phase eye velocity of the response (units °/s) to the probe (or sine) component of the PSS stimulus during the portion of the PSS when the step component is leftward-moving.
- $R_R$=peak slow phase eye velocity of the response to the probe (or sine) component of the PSS stimulus during the portion of the PSS when the step component is rightward-moving.
- $S_L$=peak amplitude the probe (or sine) component (units °/s) of the PSS stimulus during the portion of the PSS when the step component is leftward-moving.
- $S_R$=peak amplitude the probe (or sine) component (units °/s) of the PSS stimulus during the portion of the PSS when the step component is rightward-moving.

Nominally, $S_R = S_L$. The peak slow phase eye velocity values, $R_L$ and $R_R$, are derived from a curve fit of a sinusoidal function to the average probe-component eye velocity. The expectation is that the sine component asymmetry parameter will have a positive value for a patient with right side vestibular loss, a negative value for a patient with left side vestibular loss, and a value close to zero for subjects with normal vestibular function.

The measures shown in FIGS. 17A-17B were used to determine response parameter variation with PSS amplitude for the subjects of the PSS stimulus test. In the normal subjects, the step component asymmetry and sine component symmetry measures were tightly distributed about zero. The step component slopes were greater than $4°/s^2$ for most normal subjects, indicating that their VOR time constants were greater than 5 s. Exceptions were on a normal subject with poor quality data (VOR suppression) and one overly tested normal subject.

For the unilateral loss subjects, the step component asymmetry and sine component asymmetry measures generally indicated the side of vestibular dysfunction and were distinguishable from normal subject results even with the smallest amplitude PSS stimulus. Differences between normal and unilateral loss subjects increased with increasing PSS amplitude. The step component slopes were closer to zero than for most normal subjects, indicating that unilateral loss subjects have smaller VOR time constants compared to normal subjects.

For the asymmetric bilateral loss subject, both step component and sine component asymmetry measures indicated the side of greater vestibular loss, but the step component asymmetry measure showed larger deviation from normal. The step component slope measure was negative and lower than either normal or unilateral loss subjects, consistent with a reduced VOR time constant (<5 s).

The results showed that the PSS rotation stimulus can reveal asymmetric VOR responses in subjects with unilateral and with asymmetric bilateral vestibular loss. Three VOR response measures were developed that distinguished between unilateral vestibular loss and normal subjects. Two of the measures were able to reliably identify the dysfunctional ear. The third VOR response measure provided information about the VOR time constant which is known to be reduced in unilateral vestibular loss subjects, and further reduced in bilateral vestibular loss subjects. The large amplitude rotational motions required for the PSS stimulus were well tolerated by all subjects. The large amplitude rotations theoretically enhance ability to distinguish between normal and unilateral loss subjects, but also result in decreased accuracy of VOR response estimates due to the presence of high frequency nystagmus. It is likely that PSS stimuli with peak velocities in the range of 150-225°/s will provide for optimal identification of asymmetric vestibular function.

A VOR Fixation Suppression Rotation Test Based on the Bias-Probe Rotation Test.

The same rotational stimuli (2-sine stimulus and PSS stimulus) that are used for the Bias-Probe rotation test performed in the dark can also be used with a visual fixation light. This version of the Bias-Probe rotation test is performed using a single fixation light placed in front of the subject, where this light rotates with the subject. The room in which this test is performed is otherwise dark. The purpose of using a visual fixation light is to partially suppress the eye movements evoked by the vestibulo-ocular reflex (VOR). The advantage of partially suppressing the VOR is that lower velocity eye movements are obtained that are often more consistent over time (compared to the VOR eye movements obtained in the dark). VOR eye movements are "consistent" when they show a continuous relationship to the rotational stimulus velocity. More consistent eye movements provide more reliable measures that are better able to distinguish between normal and abnormal vestibular function.

Figure 18A:
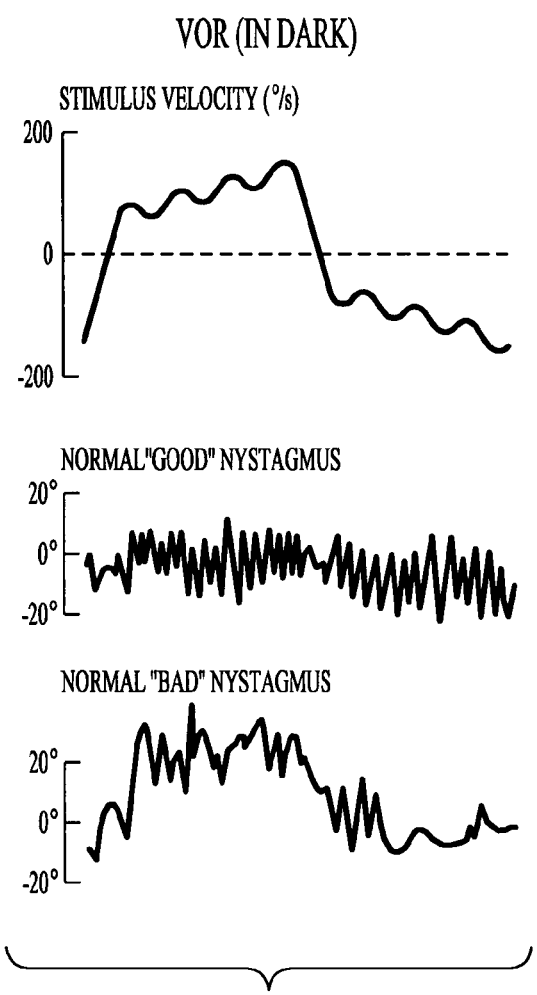
FIGS. 18A-18B show eye movement data in normal subjects measured in the dark and measured with a light fixation for an embodiment of a PSS rotational stimulus, in accordance with the teachings of the present invention.
Figure 18B:
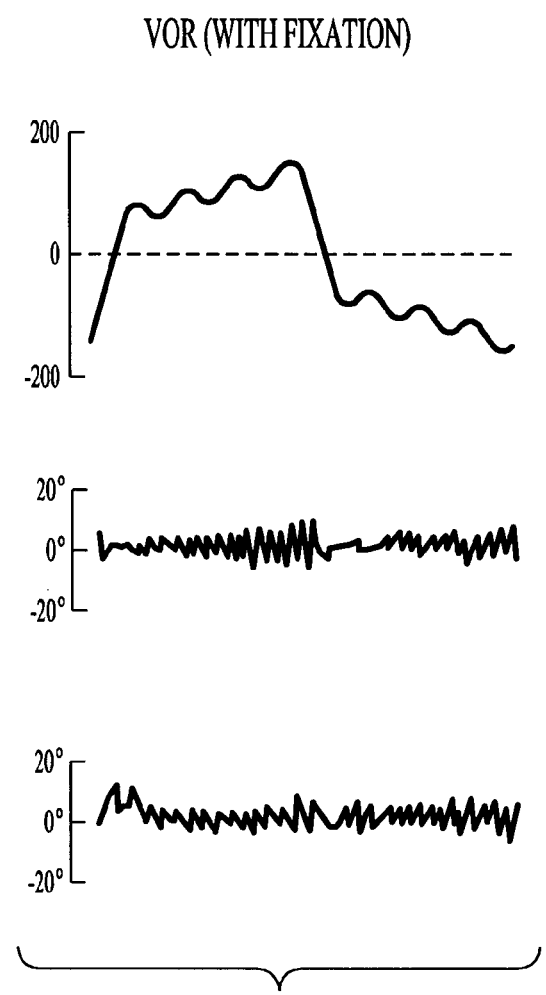
Figure 19A:
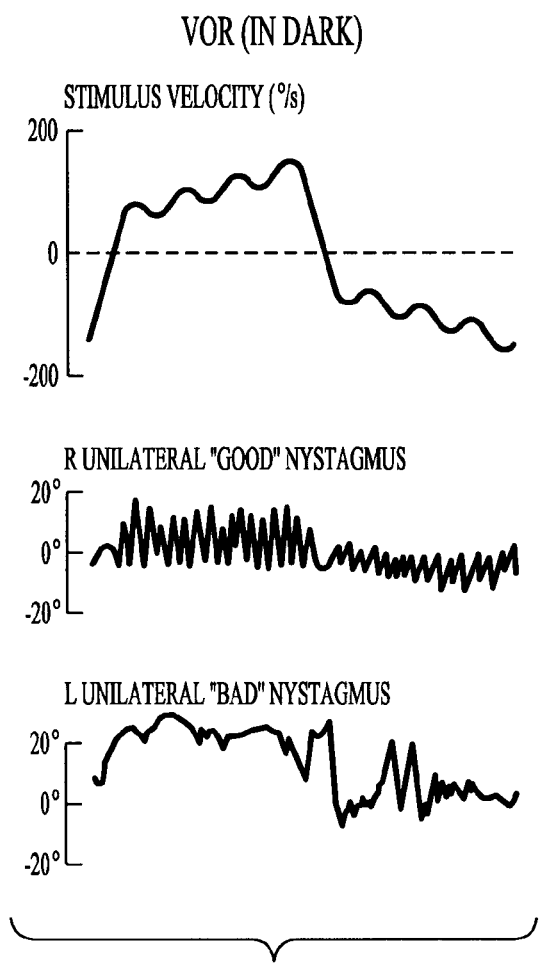
FIGS. 19A-19B show eye movement data in subjects with unilateral vestibular loss measured in the dark and measured with a light fixation for an embodiment of a PSS rotational stimulus, in accordance with the teachings of the present invention.
Figure 19B:
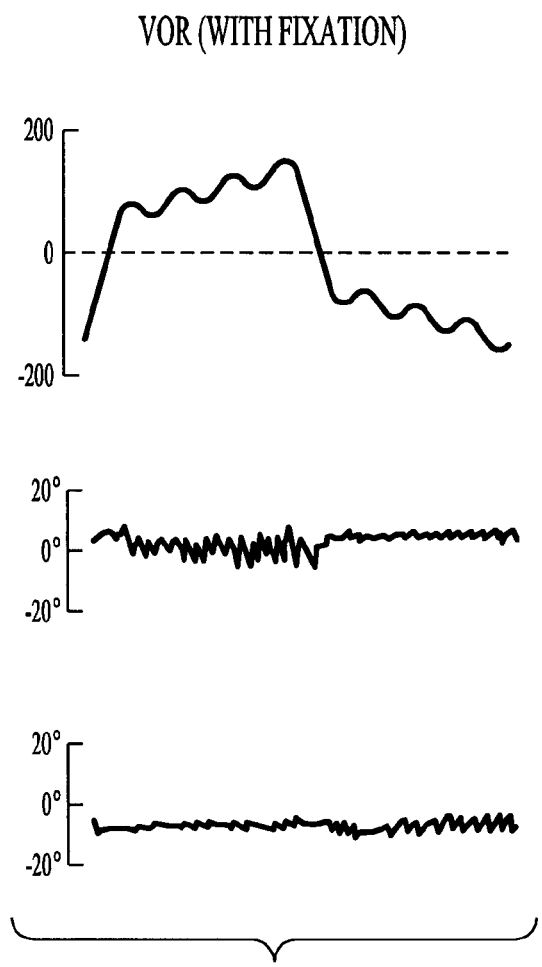

Example eye movement data from two normal subjects are shown in FIGS. 18A-18B. One of these normal subjects (middle trace of FIG. 18A) had "good" nystagmus (eye movements) during a PSS stimulus performed in the dark, and the other subject (lower trace of FIG. 18A) had "bad" nystagmus. The distinguishing feature of good versus bad nystagmus is the consistency of the eye movements over time and the relationship of the eye movements to the stimulus rotation. When the test was repeated with the fixation light, the nystagmus was partially suppressed in the subject with good nystagmus, but remained consistent over time (middle trace of FIG. 18B). When the test was repeated with the fixation light for the subject with bad nystagmus in the dark, the nystagmus became consistent over time (lower trace of FIG. 18B). Similar results are shown in FIGS. 19A-19B for two patients with a unilateral vestibular loss. The patient with a right unilateral loss (middle traces of FIGS. 19A-19B) had consistent nystagmus on PSS tests performed in both the dark and with the fixation light. The patient with a left unilateral loss had inconsistent nystagmus in the dark (lower trace of FIG. 19A), but consistent nystagmus when tested with the fixation light (lower trace of FIG. 19B).

Also evident in FIGS. 19A-19B showing the VOR with fixation for the unilateral vestibular loss patients, there is a large asymmetry between eye movements evoked during rotation to the left (positive PSS stimulus velocity) versus rotation to the right (negative PSS stimulus velocity). The eye movements evoked by Bias-Probe rotation tests with fixation can be analyzed using the same principles and methods developed for the analysis of Bias-Probe rotation tests performed in the dark. Specifically, the slow-phase velocity eye movement responses to the bias component and the probe component can be separated from one another, and curve fits performed to estimate parameters that characterize vestibular function and response symmetry. This applies for both the 2-sine and PSS rotational stimuli.

Unilateral vestibular loss patients show two types of VOR fixation asymmetries not present in normal subjects. First, unilateral vestibular loss patients are better able to visually suppress VOR eye movements during bias component rotation toward the dysfunctional ear than during rotation toward the intact ear because the total change in semicircular canal afferent nerve discharge rate is lower during rotation toward the dysfunctional ear than during rotation toward the intact ear. Second, VOR responses caused by the probe component are absent or reduced during the portion of the rotation stimulus when the patient is rotating toward the dysfunctional ear because canal afferent activity is silenced in the intact ear and the dysfunctional ear is unable to encode the probe component stimulus.

Figure 20B:
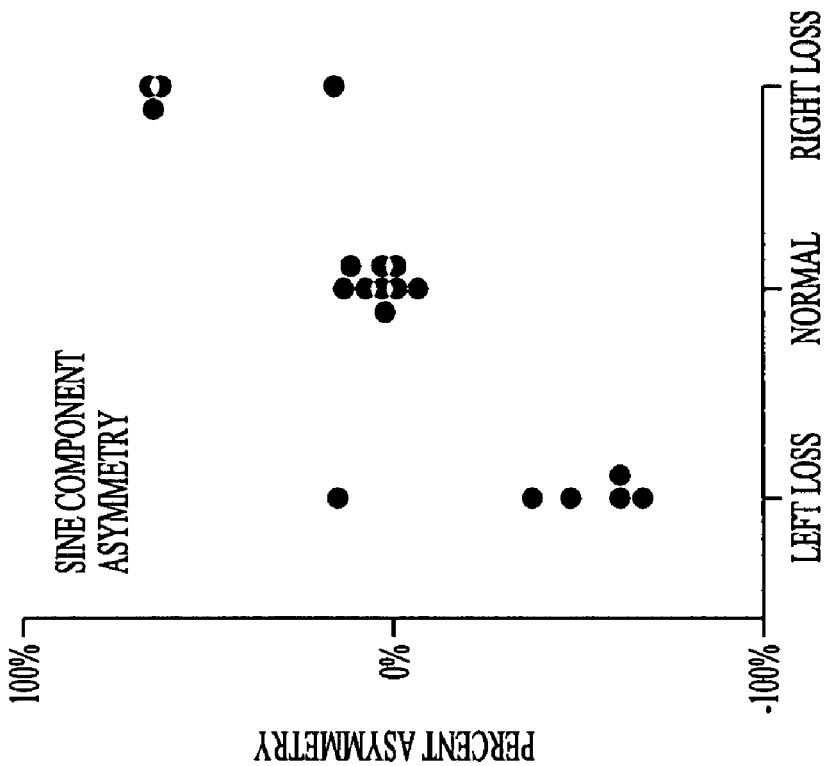
FIGS. 20A-20B show response parameters obtained from a fixation test performed on subjects with normal vestibular function and patients with unilateral vestibular loss for an embodiment of a PSS rotational stimulus, in accordance with the teachings of the present invention.
Figure 20A:
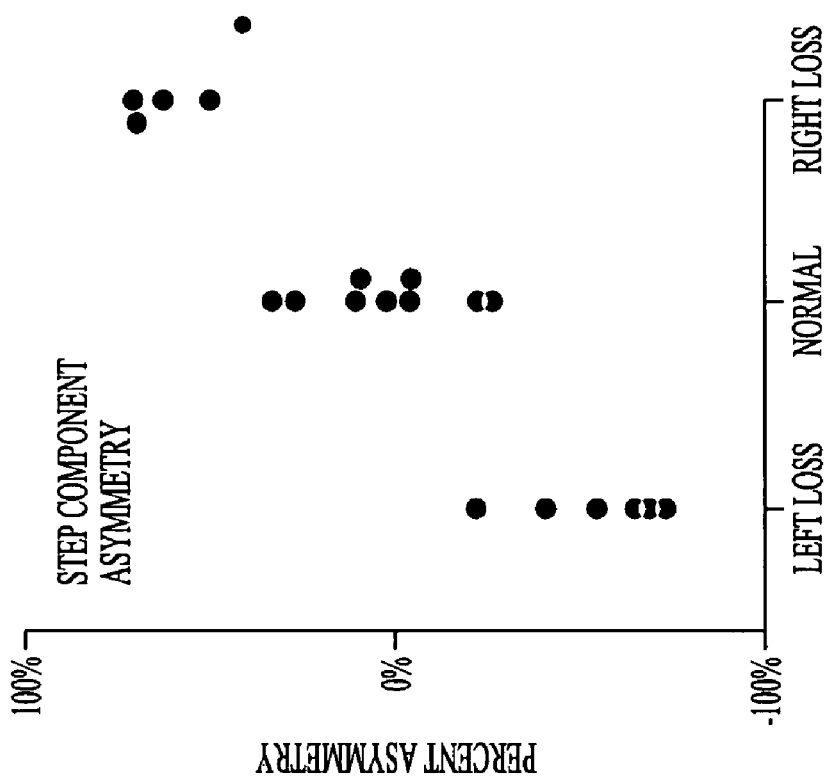

Response parameters obtained from fixation test performed on subject with normal vestibular function and patients with unilateral vestibular loss subjects are shown in FIGS. 20A-20B. FIG. 20A shows a "step component asymmetry" measure that refers to a measure obtained from the response to the bias component of the PSS stimulus. FIG. 20B shows a "sine component asymmetry" measure that refers to a measure obtained from the response to the probe component of the PSS stimulus. In nearly all cases, these measures provided a good separation of normal subjects from patients with a unilateral vestibular loss. The two cases were the sine component asymmetry measure did not provide a good separation between normal and unilateral loss are attributable to unilateral loss subjects who were able to nearly completely suppress their VOR using the fixation light.

CONCLUSION

The limitations with the current vestibular function tests indicate that no single test thus far adequately answers the most important diagnostic questions in the evaluation of vestibular function: (1) Is vestibular function normal or abnormal? (2). If abnormal, which ear is affected, or are both ears affected? (3) How severe is the abnormality?

The inadequacy of the existing tests can be partially resolved by performing multiple tests on the same patient, using a combination of the existing tests. However, some patients, due to their physical limitations cannot tolerate certain of the tests (e.g. head pulse test), and in any case, multiple tests increase the cost of obtaining a diagnosis. In practice, physicians usually settle for a single test, and the referred test has been the caloric test with all of its attendant limitations.

Various embodiments for methods and apparatus according to the teachings of the present invention provide rotation test and analysis that overcome many of the poor performance features found in existing tests and provides a new diagnostic tool to identify normal and abnormal vestibular function, to localize an abnormality to a particular ear, and to evaluate the severity of the abnormality. This information is critical for the physician s delivery of therapies targeted to the patient's specific vestibular condition.

In embodiments, the use of rotational motions with amplitudes larger than typically used in conventional clinical rotation tests can reveal asymmetric VOR responses in subjects with unilateral vestibular loss. This VOR asymmetry can be reliably measured and used to identify the dysfunctional ear. The VOR asymmetry is revealed as a saturation nonlinearity during rotations towards the absent ear. Rotational motions greater than about 150°/s are sufficient to quantify the VOR saturation amplitude in unilateral loss subjects. The inclusion of a high frequency, low amplitude probe component in the rotational stimulus provides a second measure that identifies the presence and side of abnormal vestibular functions. The larger amplitude rotational motions required for the two-sine and PSS stimuli were well tolerated by tested subjects. Optimal test sensitivity may be achieved when the head is oriented with the canal planes perpendicular to the rotation axis. However, it may be difficult to achieve this optimal orientation in each subject since external landmarks are not tightly correlated with canal orientation. Large amplitude rotations enhanced the ability to distinguish between normal and unilateral loss subjects, but also resulted in decreased accuracy of VOR response estimates due to the presence of high frequency nystagmus. It is likely that a bias component peak velocity in the range of 150-200°/s will provide for optimal identification of asymmetric vestibular function.

The invention has been described with reference to various specific and preferred embodiments and techniques. However, it should be understood that many variations and modifications may be made while remaining within the spirit and scope of the invention. Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. It is to be understood that the above description is intended to be illustrative, and not restrictive. Combinations of the above embodiments, and other embodiments will be apparent to those of skill in the art upon reviewing the above description. The scope of the invention includes any other applications in which the above structures and fabrication methods are used.

What is claimed is:

1. A system comprising:
an eye velocity computing unit arranged such that the eye velocity computing unit operatively computes eye velocity from eye position data from a subject as a result of applying a stimulus to control rotational motion of the subject to affect vestibular responses of the subject, the stimulus having a bias component and a probe component such that vestibular responses in one ear of the subject are temporarily turned off during application of the bias component with the probe component modulating the bias component to evaluate responsiveness in another ear of the subject; and
a filter arranged such that the filter operatively isolates and separates a bias response to the bias component of the stimulus from a probe response to the probe component of the stimulus to analyze separately the bias response and the probe response.

2. The system of claim 1, wherein the filter includes a bandpass filter arranged such that the bandpass filter operatively filters a slow phase eye velocity in isolating the probe response providing a bandpass slow phase eye velocity.

3. The system of claim 2, wherein the system includes tools that parameterize the probe response including tools that curve fit an averaged bandpass slow phase eye velocity, $\hat{\theta}_{bp}$, the curve fit related to a probe frequency, $\omega_p$, and a bias frequency, $\omega_b$, and having a probe component eye velocity amplitude, $A_p$, a probe component phase, $\phi_p$, a phase of the modulation waveform, $\phi_b$, and a modulation factor, m, that varies from 0 to 1, as fit parameters.

4. The system of claim 3, wherein the curve fit includes a curve fit according to the relation $$\langle\hat{\theta}_{bp}\rangle = A_p(1+m\cos(\omega_b t+\phi_b))\cos(\omega_p t+\phi_p).$$

5. The system of claim 1, wherein the system includes:
a first low pass filter arranged such that the first low pass filter operatively filters a slow phase eye velocity operatively removing the probe response to provide an isolated bias component of the eye velocity;
a second low pass filter arranged such that the second low pass filter operatively filters a stimulus velocity, operatively removing the probe component to provide an isolated bias component of the stimulus velocity; and
a diagnostics tool arranged such that an input-output function is operatively generated, the input-output function correlated to the isolated bias component of the eye velocity versus the isolated bias component of the stimulus velocity.

6. The system of claim 5, wherein the system is arranged such that the system operatively estimates a phase for an averaged isolated bias component and a phase for an averaged low pass slow phase eye velocity at a frequency of the bias component, and operatively time shifts the averaged isolated bias component and the averaged low pass slow phase eye velocity such that the averaged isolated bias component and the averaged low pass slow phase eye velocity are aligned with a 180° phase shift between each other.

7. The system of claim 6, wherein the system is arranged such that the system operatively determines a curve fit to the averaged low pass slow phase eye velocity, $\hat{\theta}'_{lp}$, related to the averaged low pass bias velocity, $\omega'_{lp}$, and operatively fits parameters K and β, K being related to gain behavior of the input-output function and β being related to a saturation behavior of the input-output function.

8. The system of claim 7, wherein the curve fit includes a curve fit according to the relation $$\langle\hat{\theta}'_{lp}\rangle = \frac{K\left(1-e^{-\beta(\omega'_{lp})}\right)}{1+e^{-\beta(\omega'_{lp})}}.$$

9. The system of claim 5, wherein the system is arranged such that the system operatively determines deviations of the input-output function from a straight line.

* * * * *